(12) United States Patent
Cumming et al.

(10) Patent No.: US 8,067,642 B2
(45) Date of Patent: Nov. 29, 2011

(54) CHIRAL PHOSPHOROUS COMPOUNDS

(75) Inventors: Graham R. Cumming, Co. Dublin (IE); Declan Gilheany, Dublin (IE); Gary King, Dublin (IE); Matthias Voegler, Dublin (IE); Vladimir Larichev, Margate (GB)

(73) Assignee: Celtice Catalysts Limited, Nova UCD, Dublin (IE)

( * ) Notice: Subject to any disclaimer, the term of this patent is extended or adjusted under 35 U.S.C. 154(b) by 0 days.

(21) Appl. No.: 12/593,292

(22) PCT Filed: Mar. 28, 2008

(86) PCT No.: PCT/GB2008/001053
§ 371 (c)(1),
(2), (4) Date: Feb. 26, 2010

(87) PCT Pub. No.: WO2008/117054
PCT Pub. Date: Oct. 2, 2008

(65) Prior Publication Data
US 2010/0168456 A1 Jul. 1, 2010

(30) Foreign Application Priority Data
Mar. 28, 2007 (GB) .................. 0707379.4

(51) Int. Cl.
*C07F 9/92* (2006.01)
(52) U.S. Cl. .............................. 568/17; 568/2
(58) Field of Classification Search .......... None
See application file for complete search history.

(56) References Cited

U.S. PATENT DOCUMENTS
4,008,281 A * 2/1977 Knowles et al. .......... 568/13
4,230,641 A * 10/1980 Bartish .................. 568/454

FOREIGN PATENT DOCUMENTS
GB 1466803 3/1977

OTHER PUBLICATIONS

Wada et al., {Optically Pure 1,2-Bis[(o-alkylphenyl)phenylphosphino]ethanes and Their Use in Rhodium-Catalyzed Asymmetric Hydrogenations of e-(Acylamino)acrylic Derivatives, Adv. Synth. Catal. 2004, 346, 777-788.*
Casey et al., {Electronically Dissymmetric DIPHOS Derivatives Give Higher n:i Regioselectivity in Rhodium-Catalyzed Hydroformylation Than Either of Their Symmetric Counterparts, J. Am. Chem. Soc. 1999, 121, 63-70}.*
Chatt et al., {The preparation and properties of some diphosphines R2PCH2CH2PR2 (R=alkyl or aryl) and of their rhenium(I) dinitrogen derivatives, Journal of the Chemical Society, Dalton Transactions: Inorganic Chemistry (1972-1999) (1985), (6), 1131-6}.*
Brunner, H. et al., "Asymmetrische Katalysen, 88[1]. Kinetik der Rh-katalysierten Hydrierung von (Z)-( α)-(N)-Acetylaminozimtsaure mit optisch aktiven Schalenphosphinen als Liganden," *Zeitschrift Fur Naturforschung, Teil B:Anorganische Chemie, Organische Chemie*, vol. 49, No. 9 (1994), pp. 1305-1307. XP000466909.
Brunner, H. et al., "Enantioselektive Katalyse. LXXXI. Optisch aktive Zweischalenphosphine," *Journal of Organometallic Chemistry*, vol. 454, No. 1/02 (1993), pp. 87-94. XP000576108.
Casey, C.P. et al., "Electronically Dissyemetric DIPHOS Derivatives Give Higher n:i Regioselectivity in Rhodium-Catalyzed Hydroformylation Than Either of Their Symmetric Counterparts," *Journal of the American Chemical Society*, vol. 121, No. 1 (1999), pp. 63-70. XP000789493.
Crepy, K.V.L. et al., "Recent Developments in Catalytic Asymmetric Hydrogenation Employing P-Chirogenic Diphosphine Ligands," *Advanced Synthesis and Catalysis*, vol. 345, No. 1-2 (2003), pp. 79-101. XP009060886. Kagan, H.B., "Asymmetric Catalysis in Organic Synthesis with Industrial Perspectives," *Bulletin de la Societe Chimique de France*, No. 5 (1988), pp. 846-853. XP009103754.
Knowles, W.S., "Application of Organometallic Catalysis to the Commercial Production of L-DOPA," *Journal of Chemical Education*, vol. 63 (1986), pp. 222-225. XP009103627.
Wada, Y. et al., "Opticaly Pure 1,2-Bis[(o-alkylphenyl)phenylphosphino]ethanes and Their Use in Rhodium-Catalyzed Asymmetric Hydrogenations of α-(Acylamino)acrylic Derivatives," *Advanced Synthesis and Catalysis*, vol. 346, No. 7 (2004), pp. 777-778. XP007905279.

* cited by examiner

*Primary Examiner* — Paul A Zucker
(74) *Attorney, Agent, or Firm* — Steptoe & Johnson LLP

(57) ABSTRACT

The present invention provides P-chiral compounds of general formulae (II) and (III): in formula (II) at least one of $R_{21}$, $R_{25}$, $R_{26}$ and $R_{30}$ is independently selected from CM alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; at least one of $R_{22}$, $R_{24}$, $R_{27}$ and $R_{29}$ are independently selected from $C_{1-14}$ alkyl, $CF_3$, $C_{1-14}$ alkoxy, phenyl and benzyloxy and the remaining substituents selected, from $R_{22}$, $R_{24}$, $R_{27}$ and $R_{29}$ are hydrogen; and $R_{23}$ and R28 are independently selected from hydrogen, CM alkyl, $CF_3$, $C_{1-14}$ alkoxy, phenyl and benzyloxy; in formula (III) at least one of $R_{21}$, $R_{25}$, $R_{26}$ and $R_{30}$ is independently selected from phenyl and benzyloxy and the remaining substituents selected from $R_{21}$, $R_{25}$, $R_{-26}$ and $R_{30}$ are hydrogen; and $R_{22}$, $R_{-23}$ $R_{24}$, $R_{27}$, $R_{28}$ and $R_{29}$ are independently selected from hydrogen, $C_{1-14}$ alkyl, $CF_3$, $C_{1-14}$ alkoxy, phenyl and benzyloxy.

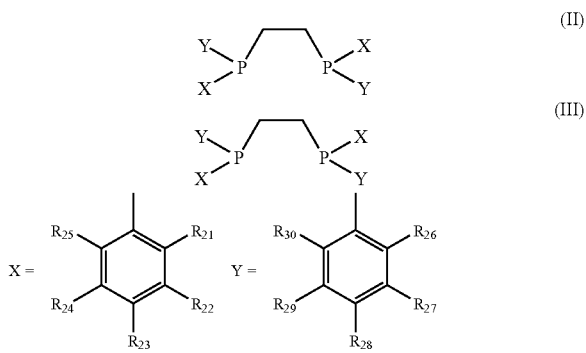

31 Claims, No Drawings

CHIRAL PHOSPHOROUS COMPOUNDS

CLAIM OF PRIORITY

This application claims priority under 35 USC 371 to International Application No. PCT/GB2008/001053, filed on Mar. 28, 2008, which claims priority to British Application Serial No. 0707379.4, filed on Mar. 28, 2007, each of which is incorporated by reference in its entirety.

FIELD OF THE INVENTION

The present invention relates to chiral phosphorus containing compounds useful in asymmetric synthesis.

BACKGROUND TO THE INVENTION

The use of chiral phosphorus compounds for catalytic asymmetric synthesis has grown enormously in the last three decades, such compounds providing many of the most successful ligands for metal-based catalysts (Ojima, 2000; Brunner et al., 1993).

Asymmetric reactions making use of metal catalysts with chiral phosphine ligands include alkene hydrogenations, hydroformylations and hydrosilylations, allylamine isomerisations, allylic substitutions and a number of cross coupling procedures. Some of these processes have gained industrial significance, e.g. Monsanto's L-dopa process (Knowles, 1986); Anic and Monsanto Aspartame process (Kagan, 1988) and Syntex naproxen process (Noyori, 1989). Chiral phosphorus compounds have been found to be useful non-metallic catalysts in their own right (Noyori, 1989).

An important sub-set of chiral phosphorus compounds are those where the chirality lies at the phosphorus atom itself, referred to as P-chiral (or P-stereogenic) compounds. P-chiral compounds have proven to be particularly useful in catalytic asymmetric syntheses (Crépy, K. V. L.; Imamoto, T. Adv. Synth. Catal. 2003, 345, 79-101). An example of such a P-chiral compounds useful in catalytic asymmetric synthesis is shown in the rhodium/diPAMP catalyst, developed by Knowles, which is one of the most successful catalysts used for the L-dopa and Aspartame syntheses.

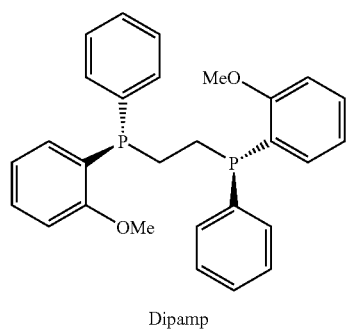

Dipamp

In light of the potential beneficial properties of P-chiral phosphorus compounds in asymmetric synthesis, there is an ongoing need for further such compounds.

STATEMENTS OF THE INVENTION

According to a first aspect of the present invention there is provided a P-chiral compound of general formula (II):

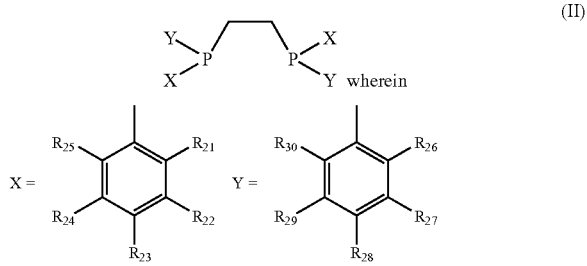

wherein at least one of $R_{21}$, $R_{25}$, $R_{26}$ and $R_{30}$ is independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; at least one of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen; and $R_{23}$ and $R_{28}$ are independently selected from hydrogen, $C_{1-4}$ alkyl, $CF_3$, $C_{1-4}$ alkoxy, phenyl and benzyloxy.

According to another aspect of the present invention there is provided a P-chiral compound of general formula (III):

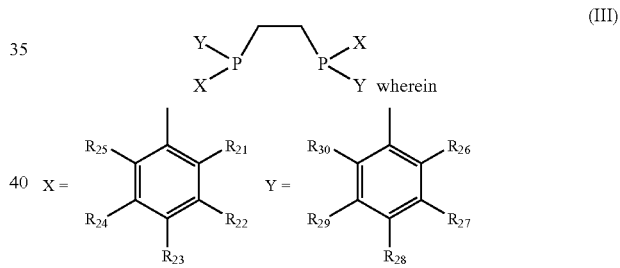

wherein at least one of $R_{21}$, $R_{25}$, $R_{26}$ and $R_{30}$ is independently selected from phenyl and benzyloxy and the remaining substituents selected from $R_{21}$, $R_{25}$, $R_{26}$ and $R_{30}$ are hydrogen; and $R_{22}$, $R_{23}$, $R_{24}$, $R_{27}$, $R_{28}$ and $R_{29}$ are independently selected from hydrogen, $C_{1-4}$ alkyl, $CF_3$, $C_{1-4}$ alkoxy, phenyl and benzyloxy.

In a further aspect, the present invention provides a process for the preparation of a P-chiral compound of general formula (II) or general formula (III) which comprises reducing a P-chiral compound of formula (XII):

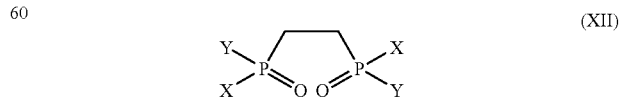

In a further aspect, the present invention provides a process for the preparation of a P-chiral compound of general formula (II) or general formula (III) which comprises reducing a P-chiral compound of formula (XIII):

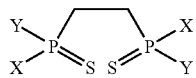
(XIII)

In a further aspect, the present invention provides a process for the preparation of a P-chiral compound of general formula (II) or general formula (III) which comprises deboronating a P-chiral compound of formula (XIV):

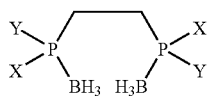
(XIV)

In a further aspect, the present invention provides a transition metal complex comprising a P-chiral compound of general formula (II) or general formula (III).

In a further aspect, the present invention provides the use of a P-chiral compound of general formula (II) or general formula (III) in chiral synthesis.

DETAILED DESCRIPTION

In the following, compounds identified as having particular benefit as ligands for use in chiral catalysis are those of formula (II) or (III) having at least one meta substituent on X or Y or at least one bulky ortho substituent (phenyl or benzyloxy).

According to a first aspect of the present invention there is provided a P-chiral compound of general formula (II):

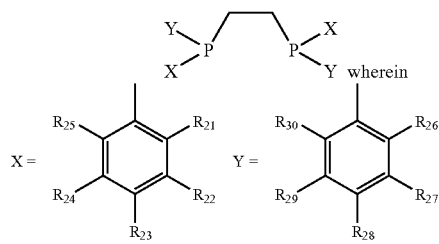
(II)

wherein at least one of $R_{21}$, $R_{25}$, $R_{26}$ and $R_{30}$ is independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; at least one of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen; and $R_{23}$ and $R_{28}$ are independently selected from hydrogen, $C_{1-4}$ alkyl, $CF_3$, $C_{1-4}$ alkoxy, phenyl and benzyloxy.

In one embodiment of the compounds of general formula (II), $R_{21}$, $R_{25}$, $R_{26}$ and $R_{30}$ are independently selected from $C_{1-4}$ alkyl, $CF_3$, $C_{1-4}$ alkoxy, phenyl and benzyloxy.

In one embodiment of the compounds of general formula (II), three of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen.

In one embodiment of the compounds of general formula (II), two of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen.

In one embodiment of the compounds of general formula (II), one of $R_{21}$, $R_{25}$, $R_{26}$ and $R_{30}$ is independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen.

In one embodiment of the compounds of general formula (II), $R_{22}$, $R_{24}$, $R_{27}$ and $R_{29}$ are independently selected from $C_{1-4}$ alkyl, $CF_3$, $C_{1-4}$ alkoxy, phenyl and benzyloxy.

In one embodiment of the compounds of general formula (II), three of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituent selected from $R_{22}$, $R_{24}$, $R_{27}$ and $R_{29}$ is hydrogen.

In one embodiment of the compounds of general formula (II), two of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), one of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), $R_{21}$, $R_{25}$, $R_{26}$ and $R_{30}$ are independently selected from $C_{1-4}$ alkyl, $CF_3$, $C_{1-4}$ alkoxy, phenyl and benzyloxy; and $R_{22}$, $R_{24}$, $R_{27}$ and $R_{29}$ are independently selected from $C_{1-4}$ alkyl, $CF_3$, $C_{1-4}$ alkoxy, phenyl and benzyloxy.

In one embodiment of the compounds of general formula (II), $R_{21}$, $R_{25}$, $R_{26}$ and $R_{30}$ are independently selected from $C_{1-4}$ alkyl, $CF_3$, $C_{1-4}$ alkoxy, phenyl and benzyloxy; and three of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituent selected from $R_{22}$, $R_{24}$, $R_{27}$ and $R_{29}$ is hydrogen.

In one embodiment of the compounds of general formula (II), $R_{21}$, $R_{25}$, $R_{26}$ and $R_{30}$ are independently selected from $C_{1-4}$ alkyl, $CF_3$, $C_{1-4}$ alkoxy, phenyl and benzyloxy; and two of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), $R_{21}$, $R_{25}$, $R_{26}$ and $R_{30}$ are independently selected from $C_{1-4}$ alkyl, $CF_3$, $C_{1-4}$ alkoxy, phenyl and benzyloxy; and one of $R_{22}$, $R_{24}$, $R_{27}$ and $R_{29}$ is independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), three of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituent selected from $R_{21}$, $R_{25}$, $R_{26}$ and $R_{30}$ is hydrogen; and $R_{22}$, $R_{24}$, $R_{27}$ and $R_{29}$ are independently selected from $C_{1-4}$ alkyl, $CF_3$, $C_{1-4}$ alkoxy, phenyl and benzyloxy.

In one embodiment of the compounds of general formula (II), three of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituent selected from $R_{21}$, $R_{25}$, $R_{26}$ and $R_{30}$ is hydrogen; and three of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituent selected from $R_{22}$, $R_{24}$, $R_{27}$ and $R_{29}$ is hydrogen.

In one embodiment of the compounds of general formula (II), three of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituent selected from $R_{21}$, $R_{25}$, $R_{26}$ and $R_{30}$ is hydrogen; and two of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), three of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituent selected from $R_{21}$, $R_{25}$, $R_{26}$ and $R_{30}$ is hydrogen; and one of $R_{22}$, $R_{24}$, $R_{27}$ and $R_{29}$ is independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), two of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; and $R_{22}$, $R_{24}$, $R_{27}$ and $R_{29}$ are independently selected from $C_{1-4}$ alkyl, $CF_3$, $C_{1-4}$ alkoxy, phenyl and benzyloxy.

In one embodiment of the compounds of general formula (II), two of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; and three of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituent selected from $R_{22}$, $R_{24}$, $R_{27}$ and $R_{29}$ is hydrogen.

In one embodiment of the compounds of general formula (II), two of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; and two of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), two of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; and one of $R_{22}$, $R_{24}$, $R_{27}$ and $R_{29}$ is independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), one of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; and $R_{22}$, $R_{24}$, $R_{27}$ and $R_{29}$ are independently selected from $C_{1-4}$ alkyl, $CF_3$, $C_{1-4}$ alkoxy, phenyl and benzyloxy.

In one embodiment of the compounds of general formula (II), one of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; and three of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituent selected from $R_{22}$, $R_{24}$, $R_{27}$ and $R_{29}$ is hydrogen.

In one embodiment of the compounds of general formula (II), one of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; and two of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), one of $R_{21}$, $R_{25}$, $R_{26}$ and $R_{30}$ are independently selected from $C_{1-4}$ alkyl, $CF_3$, $C_{1-4}$ alkoxy, phenyl and benzyloxy and the remaining substituents selected from $R_{21}$, $R_{25}$, $R_{26}$ and $R_{30}$ are hydrogen; and one of $R_{22}$, $R_{24}$, $R_{27}$ and $R_{29}$ is independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

In one embodiment of the compounds of general formula (II), $R_{22}$ and $R_{24}$ are independently selected from $C_{1-4}$ alkyl, $CF_3$, $C_{1-4}$ alkoxy, phenyl and benzyloxy and $R_{27}$ and $R_{29}$ are hydrogen.

In one embodiment of the compounds of general formula (II), $R_{21}$ and $R_{24}$ are independently selected from $C_{1-4}$ alkyl, $CF_3$, $C_{1-4}$ alkoxy, phenyl and benzyloxy and $R_{22}$, $R_{23}$, $R_{25}$, $R_{26}$, $R_{27}$, $R_{28}$, $R_{29}$ and $R_{30}$ are hydrogen.

In one embodiment of the compounds of general formula (II), $R_{21}$ and $R_{22}$ are independently selected from $C_{1-4}$ alkyl, $CF_3$, $C_{1-4}$ alkoxy, phenyl and benzyloxy and $R_{23}$, $R_{24}$, $R_{25}$, $R_{26}$, $R_{27}$, $R_{28}$, $R_{29}$ and $R_{30}$ are hydrogen.

In one embodiment of the compounds of general formula (II), $R_{26}$ and $R_{24}$ are independently selected from $C_{1-4}$ alkyl, $CF_3$, $C_{1-4}$ alkoxy, phenyl and benzyloxy and $R_{21}$, $R_{22}$, $R_{23}$, $R_{25}$, $R_{27}$, $R_{28}$, $R_{29}$ and $R_{30}$ are hydrogen.

In one embodiment of the compounds of general formula (II), $R_{26}$ and $R_{22}$ are independently selected from $C_{1-4}$ alkyl, $CF_3$, $C_{1-4}$ alkoxy, phenyl and benzyloxy and $R_{21}$, $R_{23}$, $R_{24}$, $R_{25}$, $R_{27}$, $R_{28}$, $R_{29}$ and $R_{30}$ are hydrogen.

In one embodiment of the compounds of general formula (II), $R_{21}$, $R_{22}$ and $R_{24}$ are independently selected from $C_{1-4}$ alkyl, $CF_3$, $C_{1-4}$ alkoxy, phenyl and benzyloxy and $R_{23}$, $R_{25}$, $R_{26}$, $R_{27}$, $R_{28}$, $R_{29}$ and $R_{30}$ are hydrogen.

In one embodiment of the compounds of general formula (II), $R_{21}$, $R_{27}$ and $R_{29}$ are independently selected from $C_{1-4}$ alkyl, $CF_3$, $C_{1-4}$ alkoxy, phenyl and benzyloxy and $R_{22}$, $R_{23}$, $R_{24}$, $R_{25}$, $R_{26}$, $R_{28}$ and $R_{30}$ are hydrogen.

In one embodiment of the compounds of general formula (II), $R_{21}$, $R_{22}$, $R_{24}$ and $R_{29}$ are independently selected from $C_{1-4}$ alkyl, $CF_3$, $C_{1-4}$ alkoxy, phenyl and benzyloxy and $R_{23}$, $R_{25}$, $R_{26}$, $R_{27}$, $R_{28}$ and $R_{30}$ are hydrogen.

In one embodiment of the compounds of general formula (II), $R_{21}$, $R_{22}$, $R_{27}$ and $R_{29}$ are independently selected from $C_{1-4}$ alkyl, $CF_3$, $C_{1-4}$ alkoxy, phenyl and benzyloxy and $R_{23}$, $R_{24}$, $R_{25}$, $R_{26}$, $R_{28}$ and $R_{30}$ are hydrogen.

In one embodiment of the compounds of general formula (II), $R_{21}$, $R_{24}$, $R_{27}$ and $R_{29}$ are independently selected from $C_{1-4}$ alkyl, $CF_3$, $C_{1-4}$ alkoxy, phenyl and benzyloxy and $R_{22}$, $R_{23}$, $R_{25}$, $R_{26}$, $R_{28}$ and $R_{30}$ are hydrogen.

In one embodiment of the compounds of general formula (II), $R_{21}$, $R_{22}$, $R_{24}$, $R_{27}$ and $R_{29}$ are independently selected from $C_{1-4}$ alkyl, $CF_3$, $C_{1-4}$ alkoxy, phenyl and benzyloxy and $R_{23}$, $R_{25}$, $R_{26}$, $R_{28}$ and $R_{30}$ are hydrogen.

In one embodiment of the compounds of general formula (II), $R_{21}$, $R_{23}$ and $R_{24}$ are independently selected from $C_{1-4}$ alkyl, $CF_3$, $C_{1-4}$ alkoxy, phenyl and benzyloxy and $R_{22}$, $R_{25}$, $R_{26}$, $R_{27}$, $R_{28}$, $R_{29}$ and $R_{30}$ are hydrogen.

In one embodiment of the compounds of general formula (II), $R_{21}$, $R_{22}$ and $R_{23}$ are independently selected from $C_{1-4}$ alkyl, $CF_3$, $C_{1-4}$ alkoxy, phenyl and benzyloxy and $R_{24}$, $R_{25}$, $R_{26}$, $R_{27}$, $R_{28}$, $R_{29}$ and $R_{30}$ are hydrogen.

In one embodiment of the compounds of general formula (II), $R_{23}$, $R_{24}$ and $R_{26}$ are independently selected from $C_{1-4}$ alkyl, $CF_3$, $C_{1-4}$ alkoxy, phenyl and benzyloxy and $R_{21}$, $R_{22}$, $R_{25}$, $R_{27}$, $R_{28}$, $R_{29}$ and $R_{30}$ are hydrogen.

In one embodiment of the compounds of general formula (II), $R_{22}$, $R_{23}$ and $R_{26}$ are independently selected from $C_{1-4}$ alkyl, $CF_3$, $C_{1-4}$ alkoxy, phenyl and benzyloxy and $R_{21}$, $R_{24}$, $R_{25}$, $R_{27}$, $R_{28}$, $R_{29}$ and $R_{30}$ are hydrogen.

In one embodiment of the compounds of general formula (II), $R_{21}$, $R_{22}$, $R_{23}$ and $R_{24}$ are independently selected from $C_{1-4}$ alkyl, $CF_3$, $C_{1-4}$ alkoxy, phenyl and benzyloxy and $R_{25}$, $R_{26}$, $R_{27}$, $R_{28}$, $R_{29}$ and $R_{30}$ are hydrogen.

In one embodiment of the compounds of general formula (II), $R_{21}$, $R_{23}$, $R_{27}$ and $R_{29}$ are independently selected from $C_{1-4}$ alkyl, $CF_3$, $C_{1-4}$ alkoxy, phenyl and benzyloxy and $R_{22}$, $R_{24}$, $R_{25}$, $R_{26}$, $R_{28}$ and $R_{30}$ are hydrogen.

In one embodiment of the compounds of general formula (II), $R_{21}$, $R_{22}$, $R_{23}$, $R_{24}$ and $R_{29}$ are independently selected from $C_{1-4}$ alkyl, $CF_3$, $C_{1-4}$ alkoxy, phenyl and benzyloxy and $R_{25}$, $R_{26}$, $R_{27}$, $R_{28}$ and $R_{30}$ are hydrogen.

In one embodiment of the compounds of general formula (II), $R_{21}$, $R_{22}$, $R_{23}$, $R_{27}$ and $R_{29}$ are independently selected from $C_{1-4}$ alkyl, $CF_3$, $C_{1-4}$ alkoxy, phenyl and benzyloxy and $R_{24}$, $R_{25}$, $R_{26}$, $R_{28}$ and $R_{30}$ are hydrogen.

In one embodiment of the compounds of general formula (II), $R_{21}$, $R_{23}$, $R_{24}$, $R_{27}$ and $R_{29}$ are independently selected from $C_{1-4}$ alkyl, $CF_3$, $C_{1-4}$ alkoxy, phenyl and benzyloxy and $R_{22}$, $R_{25}$, $R_{26}$, $R_{28}$ and $R_{30}$ are hydrogen.

In one embodiment of the compounds of general formula (II), $R_{21}$, $R_{22}$, $R_{23}$, $R_{24}$, $R_{27}$ and $R_{29}$ are independently selected from $C_{1-4}$ alkyl, $CF_3$, $C_{1-4}$ alkoxy, phenyl and benzyloxy and $R_{25}$, $R_{26}$, $R_{28}$ and $R_{30}$ are hydrogen.

In one embodiment of the compounds of general formula (II), $R_{21}$, $R_{24}$ and $R_{28}$ are independently selected from $C_{1-4}$ alkyl, $CF_3$, $C_{1-4}$ alkoxy, phenyl and benzyloxy and $R_{22}$, $R_{23}$, $R_{25}$, $R_{26}$, $R_{27}$, $R_{29}$ and $R_{30}$ are hydrogen.

In one embodiment of the compounds of general formula (II), $R_{21}$, $R_{22}$ and $R_{28}$ are independently selected from $C_{1-4}$ alkyl, $CF_3$, $C_{1-4}$ alkoxy, phenyl and benzyloxy and $R_{23}$, $R_{24}$, $R_{25}$, $R_{26}$, $R_{27}$, $R_{29}$ and $R_{30}$ are hydrogen.

In one embodiment of the compounds of general formula (II), $R_{24}$, $R_{26}$ and $R_{28}$ are independently selected from $C_{1-4}$ alkyl, $CF_3$, $C_{1-4}$ alkoxy, phenyl and benzyloxy and $R_{21}$, $R_{22}$, $R_{23}$, $R_{25}$, $R_{27}$, $R_{29}$ and $R_{30}$ are hydrogen.

In one embodiment of the compounds of general formula (II), $R_{22}$, $R_{26}$ and $R_{28}$ are independently selected from $C_{1-4}$ alkyl, $CF_3$, $C_{1-4}$ alkoxy, phenyl and benzyloxy and $R_{21}$, $R_{23}$, $R_{24}$, $R_{25}$, $R_{27}$, $R_{29}$ and $R_{30}$ are hydrogen.

In one embodiment of the compounds of general formula (II), $R_{21}$, $R_{22}$, $R_{24}$ and $R_{28}$ are independently selected from $C_{1-4}$ alkyl, $CF_3$, $C_{1-4}$ alkoxy, phenyl and benzyloxy and $R_{23}$, $R_{25}$, $R_{26}$, $R_{27}$, $R_{29}$ and $R_{30}$ are hydrogen.

In one embodiment of the compounds of general formula (II), $R_{21}$, $R_{27}$ $R_{28}$ and $R_{29}$ are independently selected from $C_{1-4}$ alkyl, $CF_3$, $C_{1-4}$ alkoxy, phenyl and benzyloxy and $R_{22}$, $R_{23}$, $R_{24}$, $R_{25}$, $R_{26}$ and $R_{30}$ are hydrogen.

In one embodiment of the compounds of general formula (II), $R_{21}$, $R_{22}$, $R_{24}$ $R_{28}$ and $R_{29}$ are independently selected from $C_{1-4}$ alkyl, $CF_3$, $C_{1-4}$ alkoxy, phenyl and benzyloxy and $R_{23}$, $R_{25}$, $R_{26}$, $R_{27}$ and $R_{30}$ are hydrogen.

In one embodiment of the compounds of general formula (II), $R_{21}$, $R_{22}$, $R_{27}$, $R_{28}$ and $R_{29}$ are independently selected from $C_{1-4}$ alkyl, $CF_3$, $C_{1-4}$ alkoxy, phenyl and benzyloxy and $R_{23}$, $R_{24}$, $R_{25}$, $R_{26}$ and $R_{30}$ are hydrogen.

In one embodiment of the compounds of general formula (II), $R_{21}$, $R_{24}$, $R_{27}$, $R_{28}$ and $R_{29}$ are independently selected from $C_{1-4}$ alkyl, $CF_3$, $C_{1-4}$ alkoxy, phenyl and benzyloxy and $R_{22}$, $R_{23}$, $R_{25}$, $R_{26}$ and $R_{30}$ are hydrogen.

In one embodiment of the compounds of general formula (II), $R_{21}$, $R_{22}$, $R_{24}$, $R_{27}$, $R_{28}$ and $R_{29}$ are independently selected from $C_{1-4}$ alkyl, $CF_3$, $C_{1-4}$ alkoxy, phenyl and benzyloxy and $R_{23}$, $R_{25}$, $R_{26}$ and $R_{30}$ are hydrogen.

In one embodiment of the compounds of general formula (II), $R_{21}$, $R_{23}$, $R_{24}$ and $R_{28}$ are independently selected from $C_{1-4}$ alkyl, $CF_3$, $C_{1-4}$ alkoxy, phenyl and benzyloxy and $R_{22}$, $R_{25}$, $R_{26}$, $R_{27}$, $R_{29}$ and $R_{30}$ are hydrogen.

In one embodiment of the compounds of general formula (II), $R_{21}$, $R_{22}$ $R_{23}$ and $R_{28}$ are independently selected from $C_{1-4}$ alkyl, $CF_3$, $C_{1-4}$ alkoxy, phenyl and benzyloxy and $R_{24}$, $R_{25}$, $R_{26}$, $R_{27}$, $R_{29}$ and $R_{30}$ are hydrogen.

In one embodiment of the compounds of general formula (II), $R_{23}$, $R_{24}$, $R_{26}$ and $R_{28}$ are independently selected from $C_{1-4}$ alkyl, $CF_3$, $C_{1-4}$ alkoxy, phenyl and benzyloxy and $R_{21}$, $R_{22}$, $R_{25}$, $R_{27}$, $R_{29}$ and $R_{30}$ are hydrogen.

In one embodiment of the compounds of general formula (II), $R_{22}$, $R_{23}$, $R_{26}$ and $R_{28}$ are independently selected from $C_{1-4}$ alkyl, $CF_3$, $C_{1-4}$ alkoxy, phenyl and benzyloxy and $R_{21}$, $R_{24}$, $R_{25}$, $R_{27}$, $R_{29}$ and $R_{30}$ are hydrogen.

In one embodiment of the compounds of general formula (II), $R_{21}$, $R_{22}$, $R_{23}$, $R_{24}$ and $R_{28}$ are independently selected from $C_{1-4}$ alkyl, $CF_3$, $C_{1-4}$ alkoxy, phenyl and benzyloxy and $R_{25}$, $R_{26}$, $R_{27}$, $R_{29}$ and $R_{30}$ are hydrogen.

In one embodiment of the compounds of general formula (II), $R_{21}$, $R_{23}$, $R_{27}$ $R_{28}$ and $R_{29}$ are independently selected from $C_{1-4}$ alkyl, $CF_3$, $C_{1-4}$ alkoxy, phenyl and benzyloxy and $R_{22}$, $R_{24}$, $R_{25}$, $R_{26}$ and $R_{30}$ are hydrogen.

In one embodiment of the compounds of general formula (II), $R_{21}$, $R_{22}$, $R_{23}$, $R_{24}$ $R_{28}$ and $R_{29}$ are independently selected from $C_{1-4}$ alkyl, $CF_3$, $C_{1-4}$ alkoxy, phenyl and benzyloxy and $R_{25}$, $R_{26}$, $R_{27}$ and $R_{30}$ are hydrogen.

In one embodiment of the compounds of general formula (II), $R_{21}$, $R_{22}$, $R_{23}$, $R_{27}$, $R_{28}$ and $R_{29}$ are independently selected from $C_{1-4}$ alkyl, $CF_3$, $C_{1-4}$ alkoxy, phenyl and benzyloxy and $R_{24}$, $R_{25}$, $R_{26}$ and $R_{30}$ are hydrogen.

In one embodiment of the compounds of general formula (II), $R_{21}$, $R_{23}$, $R_{24}$, $R_{27}$, $R_{28}$ and $R_{29}$ are independently selected from $C_{1-4}$ alkyl, $CF_3$, $C_{1-4}$ alkoxy, phenyl and benzyloxy and $R_{22}$, $R_{25}$, $R_{26}$ and $R_{30}$ are hydrogen.

In one embodiment of the compounds of general formula (II), $R_{21}$, $R_{22}$, $R_{23}$, $R_{24}$, $R_{27}$, $R_{28}$ and $R_{29}$ are independently selected from $C_{1-4}$ alkyl, $CF_3$, $C_{1-4}$ alkoxy, phenyl and benzyloxy and $R_{25}$, $R_{26}$ and $R_{30}$ are hydrogen.

In the above embodiments, when not hydrogen, $R_{21}$, $R_{22}$, $R_{23}$, $R_{24}$, $R_{25}$, $R_{26}$ $R_{27}$, $R_{28}$, $R_{29}$ and $R_{30}$ are preferably independently selected from $C_{1-4}$ alkyl, $CF_3$, $C_{1-4}$ alkoxy and benzyloxy.

In the above embodiments, when not hydrogen, $R_{21}$, $R_{22}$, $R_{23}$, $R_{24}$, $R_{25}$, $R_{26}$ $R_{27}$, $R_{28}$, $R_{29}$ and $R_{30}$ are preferably independently selected from $C_{1-4}$ alkyl, $CF_3$, $C_{1-4}$ alkoxy and phenyl.

In the above embodiments, when not hydrogen, $R_{21}$, $R_{22}$, $R_{23}$, $R_{24}$, $R_{25}$, $R_{26}$ $R_{27}$, $R_{28}$, $R_{29}$ and $R_{30}$ are preferably independently selected from $C_{1-4}$ alkyl, $CF_3$ and $C_{1-4}$ alkoxy.

In the above embodiments, when not hydrogen, $R_{21}$, $R_{22}$, $R_{23}$, $R_{24}$, $R_{25}$, $R_{26}$ $R_{27}$, $R_{28}$, $R_{29}$ and $R_{30}$ are preferably independently selected from $C_{1-4}$ alkyl and $C_{1-4}$ alkoxy.

Preferred compounds of general formula (II) are set out in the table below:

| Example | $R_{21}$ | $R_{22}$ | $R_{23}$ | $R_{24}$ | $R_{25}$ | $R_{26}$ | $R_{27}$ | $R_{28}$ | $R_{29}$ | $R_{30}$ |
|---|---|---|---|---|---|---|---|---|---|---|
| A | H | H | H | H | H | Me | Me | H | Me | H |
| B | H | H | H | H | H | OMe | Me | H | Me | H |
| C | H | H | H | H | H | Me | H | H | $CF_3$ | H |
| D | H | H | H | H | H | Me | Me | OMe | Me | H |
| E | Me | H | H | H | H | H | Me | H | Me | H |
| F | Me | H | H | H | H | H | OMe | H | OMe | H |
| G | Me | H | H | H | H | H | Me | OMe | Me | H |
| H | OMe | H | H | H | H | H | Me | H | Me | H |
| I | OMe | H | H | H | H | H | Me | OMe | Me | H |
| J | OMe | H | H | H | H | H | OMe | H | OMe | H |
| K | Me | Me | H | Me | H | H | Me | H | Me | H |
| L | Me | Me | H | Me | H | H | Me | OMe | Me | H |
| M | Me | Me | H | Me | H | H | OMe | H | OMe | H |
| N | H | H | H | H | H | OMe | H | H | OMe | H |
| O | H | H | H | H | H | OBn | H | H | H | H |
| P | H | H | H | H | H | Ph | H | H | H | H |

According to another aspect of the present invention there is provided a P-chiral compound of general formula (III):

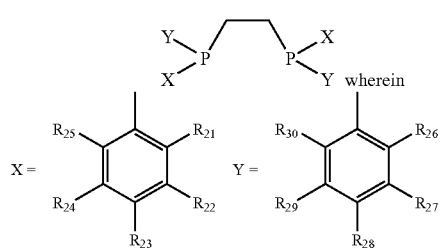

wherein at least one of $R_{21}$, $R_{25}$, $R_{26}$ and $R_{30}$ is independently selected from phenyl and benzyloxy and the remaining substituents selected from $R_{21}$, $R_{25}$, $R_{26}$ and $R_{30}$ are hydrogen; and $R_{22}$, $R_{23}$, $R_{24}$, $R_{27}$, $R_{28}$ and $R_{29}$ are independently selected from hydrogen, $C_{1-4}$ alkyl, $CF_3$, $C_{1-4}$ alkoxy, phenyl and benzyloxy.

In one embodiment of the compounds of general formula (III), one of $R_{21}$, $R_{25}$, $R_{26}$ and $R_{30}$ is independently selected from phenyl and benzyloxy and the remaining substituents selected from $R_{21}$, $R_{25}$, $R_{26}$ and $R_{30}$ are hydrogen; and $R_{22}$, $R_{23}$, $R_{24}$, $R_{27}$, $R_{28}$ and $R_{29}$ are independently selected from hydrogen, $C_{1-4}$ alkyl, $CF_3$, $C_{1-4}$ alkoxy, phenyl and benzyloxy.

In one embodiment of the compounds of general formula (III), two of $R_{21}$, $R_{25}$, $R_{26}$ and $R_{30}$ are independently selected from phenyl and benzyloxy and the remaining substituents selected from $R_{21}$, $R_{25}$, $R_{26}$ and $R_{30}$ are hydrogen; and $R_{22}$, $R_{23}$, $R_{24}$, $R_{27}$, $R_{28}$ and $R_{29}$ are independently selected from hydrogen, $C_{1-4}$ alkyl, $CF_3$, $C_{1-4}$ alkoxy, phenyl and benzyloxy.

In one embodiment of the compounds of general formula (III), $R_{22}$, $R_{23}$, $R_{24}$, $R_{27}$, $R_{28}$ and $R_{29}$ are independently selected from hydrogen, $C_{1-4}$ alkyl, $CF_3$, and $C_{1-4}$ alkoxy.

In a further embodiment of the compounds of general formula (III), one of $R_{21}$, $R_{25}$, $R_{26}$ and $R_{30}$ is independently selected from phenyl and benzyloxy and the remaining substituents selected from $R_{21}$, $R_{25}$, $R_{26}$ and $R_{30}$ are hydrogen; and $R_{22}$, $R_{23}$, $R_{24}$, $R_{27}$, $R_{28}$ and $R_{29}$ are independently selected from hydrogen, $C_{1-4}$ alkyl, $CF_3$, and $C_{1-4}$ alkoxy.

In the above embodiments of general formula (III), $R_{22}$, $R_{23}$, $R_{24}$, $R_{27}$, $R_{28}$ and $R_{29}$ are preferably independently selected from hydrogen, $C_{1-4}$ alkyl and $C_{1-4}$ alkoxy; more preferably, $R_{22}$, $R_{23}$, $R_{24}$, $R_{27}$, $R_{28}$ and $R_{29}$ are independently selected from hydrogen and $C_{1-4}$ alkyl.

The compounds of the present invention possess at least two chiral centres and therefore may exit in enantiomeric forms. The present invention covers the compounds of formula (II) in all enantiomeric forms. Preferably the compounds of the present invention are in the (R,R) configuration or in the (S,S) configuration.

As used herein, the term $C_{1-4}$ alkyl includes methyl, ethyl, n-propyl, iso-propyl, n-butyl, iso-butyl and sec-butyl. Preferably the $C_{1-4}$ alkyl group is methyl, ethyl or iso-propyl. More preferably the $C_{1-4}$ alkyl group is methyl or ethyl. Most preferably the $C_{1-4}$ alkyl group is methyl.

Optionally the $C_{1-4}$ alkyl group may be substituted with one or more halogen atoms, preferably fluorine atoms. When present there would preferably be one to five halogen atoms more preferably one to three halogen atoms, most preferably three halogen atoms. Preferred halogen substituted $C_{1-4}$ alkyl groups include trifluoromethyl.

As used herein, the term $C_{1-4}$ alkoxy includes methoxy, ethoxy, n-propoxy, iso-propoxy, n-butoxy, iso-butoxy and sec-butoxy. Preferably the $C_{1-4}$ alkoxy group is methoxy, ethoxy or iso-propoxy. More preferably the $C_{1-4}$ alkoxy group is methoxy or ethoxy. Most preferably the $C_{1-4}$ alkoxy group is methoxy.

Optionally the $C_{1-4}$ alkoxy group may be substituted with one or more halogen atoms, preferably fluorine atoms. When present there would preferably be one to five halogen atoms more preferably one to three halogen atoms, most preferably three halogen atoms. Preferred halogen substituted $C_{1-4}$ alkoxy groups include trifluoromethoxy.

The P-chiral compound of formula (XII) may be prepared by coupling a P-chiral compound of formula (XXII) with another P-chiral compound of formula (XXII):

(XXII)

Preferably the coupling reaction is a copper catalysed coupling reaction.

The P-chiral compounds of formula (XXII) may be prepared by oxidation of the corresponding racemic phosphines of formula (XXXII), using for example hydrogen peroxide, followed by resolution or chiral separation.

(XXXII)

Alternatively the P-chiral compounds of formula (XXII) may be prepared according to the methods described in WO2005118603 which is incorporated herein by reference.

The P-chiral compound of formula (XIII) may be prepared by coupling a P-chiral compound of formula (XXIII) with another P-chiral compound of formula (XXIII):

(XXIII)

Preferably the coupling reaction is a copper catalysed coupling reaction.

The P-chiral compounds of formula (XXIII) may be prepared by sulfidation of the corresponding racemic phosphines of formula (XXXII), using for example elemental sulfur, followed by resolution or chiral separation.

Alternatively the P-chiral compounds of formula (XXIII) may be prepared according to the methods described in WO2005118603 which is incorporated herein by reference.

The P-chiral compound of formula (XIV) may be prepared by coupling a P-chiral compound of formula (XXIV) with another P-chiral compound of formula (XXIV):

(XXIV)

Preferably the coupling reaction is a copper catalysed coupling reaction.

The P-chiral compounds of formula (XXII) may be prepared by boronation of the corresponding racemic phosphines of formula (XXXII), using for example hydrogen peroxide, followed by resolution or chiral separation.

Alternatively the P-chiral compounds of formula (XXIV) may be prepared by the reduction and subsequent boronation of non-racemic P-chiral compounds of formula (XXII) or (XXIII). Non-racemic (XXII) or (XXIII) may be prepared by resolution or chiral separation, or according to the methods described in WO2005118603 which is incorporated herein by reference.

Optionally, the P-chiral compounds of formula (II) or general formula (III) may be boronated to provide stable derivates suitable for longer term storage.

The compounds of the present invention may be reacted with transition metal complexes to form further transition metal complexes comprising a compound of the present invention as a ligand. Such processes are well known in the art (Ojima, 2000; Brunner et al., 1993).

In preferred transition metal complexes comprising a compound of the present invention, the transition metal is selected from rhodium, ruthenium, palladium or copper.

Examples of rhodium complexes include $[Rh(Cod)(L)]_2$, $[RhCl(L)]_2$, $[RhBr(L)]_2$, $[Rh(nbd)(L)]_2$, $[RhI(L)]_2$, $[Rh(OAc)(L)]_2$ and the like. Examples of ruthenium complexes include $[RuCl_2(L)]_2$, $[RuBr_2(L)]_2$, $[RuCl_2(L)(DMF)]_2$, $[Ru_2Cl_4(L)_2]Net_3$ and the like. Examples of palladium complexes include $[PdCl(L)]_2$, $[PdCl_2(L)]$, $[Pd(C_2H_4)L]$ and the like. Examples of copper complexes include $[Cu(OTf)_2(L)]$, $[CuCN(L)]$, $[CuI(L)]$ and the like. In the above, L is a compound of the present invention, 'cod' is cycloocta-1,5-diene and 'nbd' is norbornadiene.

The compounds of the present invention may be used in chiral synthesis, especially catalytic asymmetric hydrogenation. The compounds of the present invention may have the advantage of greater selectivity, i.e. afford compounds of greater enantiomeric purity, than similar known compounds. The compounds of the present invention may have the advantage of being effective under milder reaction conditions, particularly they may be effective at lower temperatures, than similar known compounds.

Further preferred features and embodiments of the present invention will now be described by way of non-limiting examples.

EXAMPLE 1

(R,R)-1,2-Bis[(2,5-dimethoxyphenyl)(phenyl)phosphino]ethane and (R,R)-1,2-Bis[boranato(2,5-dimethoxyphenyl)(phenyl)phosphino]ethane Step 1—1-magnesiumbromide-2,5-dimethoxybenzene To a suspension of oven dried magnesium turnings (3.1 g, 126.5 mmol) in dry THF (20 ml) under nitrogen gas was added a few crystals of iodine. A solution of 1-Bromo-2,5-dimethoxybenzene (25 g, 115 mmol) in dry THF (90 ml) was added dropwise over ~35 mins to maintain a steady reflux. Some initial heating of the suspension was required to begin the reaction. After the addition the reaction was heated to reflux and stirred for 30 mins. On cooling to ambient temperature this gave a brown solution of the Grignard, which was used immediately in the next reaction after filtration to remove some residual magnesium particles.

Step 2—Phenyl-Methyl-(2,5-dimethoxyphenyl)-phosphine

A freshly prepared solution of 1-magnesiumbromide-2,5-dimethoxybenzene (115 mmol) in THF (~110 ml) was added dropwise to phenyldichlorophosphine (15.6 ml, 115 mmol) in dry THF (300 ml) at −78° C. (acetone/dry ice bath) over a period of ~2.5 hrs. The reaction was stirred for 1 hr further at −78° C. then MeMgCl (3.0M in THF, 46 ml, 138 mmol) was added dropwise over ~30 mins. The reaction was allowed to warm to ambient temperature and stirred for a further 1 hr. The resulting phosphine is air-stable and therefore the following workup was carried out in the open air.

The solution was cooled to ~8° C. internal temperature, ice bath cooling and water (50 ml) cautiously added to destroy excess MeMgCl. Most of the THF was removed on a rotary evaporator and a further portion of water (250 ml) and diethylether (300 ml) was added. The layers were shaken and separated. The aqueous layer was extracted further with diethylether (2×100 ml). Organics combined, washed with brine (200 ml), dried (anh. $Na_2SO_4$), filtered and the solvent evaporated to give an oil. The crude phosphine was purified by a short silica plug (eluent—toluene), this gave phenyl-methyl-(2,5-dianisyl)-phosphine as a colourless oil (26.05 g, 87%).

Step 3—(R)-phenyl-methyl-(2,5-dimethoxypheny)-phosphine oxide

To a solution of phenyl-methyl-(2,5-dimethoxyphenyl)-phosphine (10.4 g, 40 mmol) in ethanol (50 ml) at ~4° C., ice bath cooling, was added 25% w/v aqueous hydrogen peroxide solution (~5 ml) dropwise over 10 mins. The solution was stirred for a further 2 hrs. After this time chloroform (100 ml) and water (100 ml) were added. The layers were shaken and separated. The aqueous layer was extracted further with chloroform (50 ml). Organics were combined, dried (anh. $Na_2SO_4$), filtered and the solvent evaporated to give phenyl-methyl-(2,5-dianisyl)-phosphine oxide (10.6 g, ~100%)

Separation of the enantiomers was achieved using a Shimadzu preparative HPLC apparatus with a Varian fraction collector model 701, AS-H Chiralpak DAIC 20345 preparative column (2 cm×25 cm), 8 ml/min flow rate, 230 nm UV detection, 80-20 pentane-EtOH mobile phase and 50 mg injections. Retention Times 13.1 min and 14.4 min for the enantiomers This procedure gave gram quantities of pure (R) & (S)-phenyl-methyl-(2,5-dimethoxyphenyl)-phosphine-oxide (ee>99%).

Step 4—(R,R)-1,2-Bis[(2,5-dimethoxyphenyl)(phenyl)phosphine oxide]ethane

A solution of LDA (4.8 mmol) in THF (4 ml) was added dropwise to a solution of pure (R)-phenyl-methyl-(2,5-dimethoxyphenyl)-phosphine oxide (1.1 g, 4 mmol) in THF (4 ml) over a period of 10 mins at 0° C., ice bath cooling. The reaction was stirred for 1 hr at 0° C. then Cu(I)Cl (480 mg, 4.8 mmol) was added, stirred for 30 mins, then Cu(II)$Cl_2$ (626 mg, 4.8 mmol) was added. The suspension was stirred for a further 30 mins at 0° C. then allowed to warm to ambient temperature and stirred for 3 hrs. After this time, conc. HCl (2 ml) was added followed by chloroform (30 ml). Layers shaken and separated. The organic layer was washed with sat. ammonium hydroxide (4×20 ml) until no further blue colour was apparent in the aqueous washings. Organic layer washed further with brine (2×20 ml), dried (anh. $Na_2SO_4$), filtered and the solvent evaporated to give an off-white solid. The crude solid was slurried in warm ethyl acetate and filtered to give pure (R,R)-1,2-Bis[(2,5-di-o-methoxyphenyl)(phenyl) phosphine oxide]ethane (570 mg, 51%, ee>99%)

Step 5—(R,R)-1,2-Bis[(2,5-dimethoxyphenyl)(phenyl)phosphino]ethane

To a solution of pure (R,R)-1,2-Bis[(2,5-dimethoxyphenyl)(phenyl)phosphine oxide]ethane (1.93 g, 3.5 mmol) and tributylamine (8.4 ml, 35 mmol) in acetonitrile (14 ml) under nitrogen gas at 70° C. was added trichlorosilane (3.15 ml, 31.15 mmol) dropwise over ~10 mins. After 2 hrs heating at 70° C. the reaction was allowed to cool to ambient temperature. The solution was added dropwise to ice cold 25% w/v NaOH (aq, 30 ml). Toluene (20 ml) was added and the layers stirred and separated. The aqueous layer was extracted further with toluene (2×10 ml). Organics were combined, washed with brine (20 ml), dried (anh. $Na_2SO_4$), filtered and the solvent evaporated to give a sticky solid. The solid was slurried in ice cold methanol (25 ml), filtered, washing with ice cold methanol. Filtrate evaporated to give pure (R,R)-1,2-Bis[(2,5-di-o-methoxyphenyl)(phenyl)phosphino]ethane (1.68 g, 93%, ee>99%)

Step 6—(R,R)-1,2-Bis[boranato(2,5-dimethoxyphenyl)(phenyl)phosphino]ethane

To pure (R,R)-1,2-Bis[(2,5-dimethoxyphenyl)(phenyl) phosphino]ethane (1.56 g, 3 mmol) in THF (20 ml) under nitrogen gas atmosphere was added borane-THF complex (1M in THF, 10 ml, 10 mmol) dropwise over ~5 mins. After 1 hr stirring at ambient temperature dilute 1M HCl (5 ml) was added carefully, followed by DCM (40 ml). Layers shaken and separated. The aqueous layer was extracted further with DCM (2×15 ml). Organics combined, washed with brine (20 ml), dried (anh. $Na_2SO_4$), filtered and the solvent evaporated to give a white solid. The solid was recrystallised from hot toluene to give pure (R,R)-1,2-Bis[boranato(2,5-dimethoxyphenyl)(phenyl)phosphino]ethane (1.05 g, 64%, ee>99%). $^1$H NMR ($CDCl_3$, 300 MHz): δ/ppm, 7.67-7.38 (12H, Ar—H, m), 6.99 (2H, Ar—H, d J=9 Hz), 6.77 (2H, Ar—H, d J=9 Hz), 3.78 (6H, —$OCH_3$, s), 3.59 (6H, —$OCH_3$, s), 2.59 (4H, —$CH_2$—P, ap. br. s); $^{31}$P NMR ($CDCl_3$, 105 MHz, $^1$H decoupled): δ/ppm, 20.6 (br. m)

(S,S) Ligand was made in a similar fashion.

EXAMPLE 2

(R,R)-1,2-Bis[phenyl-(2-benzyloxy-phenyl)phosphino]ethane and (R,R)-1,2-Bis[boranto-phenyl-(2-benzyloxy-phenyl)phosphino]ethane Step 1—(R,R)-1,2-Bis[phenyl-(2-hydroxybenzene) phosphine oxide]ethane To a solution of (R,R)-DiPAMPO (15.0 g, 30.6 mmol) in DCM (100 ml) under nitrogen gas at 0° C., ice bath cooling, was added $BBr_3$ (11.6 ml, 120 mmol) dropwise over a period of ~20 mins. The reaction became clear and was stirred overnight at ambient temperature. In the morning the reaction was quenched by the addition of water ice (~100 ml), then 2M HCl (1 L) was added. The slurry was stirred rapidly for 1 hr and then filtered, washing with water. The solid was fully dried at 70° C. under high vacuum to give pure (R,R)-1,2-Bis[phenyl-(2-hydroxybenzene)phosphine oxide]ethane (12.7 g, 90%)

Step 2—(R,R)-1,2-Bis[phenyl-(2-benzyloxy-phenyl) phosphine oxide]ethane

To a solution of (R,R)-1,2-Bis[phenyl-(2-hydroxybenzene)phosphine oxide]ethane (4.0 g, 8.6 mmol) in dry DMF (25 ml) at ambient temperature and under nitrogen atmosphere was added benzyl chloride (4.0 ml, 34.4 mmol). The reaction was heated to 40° C. and stirred for 3 days. After this time the reaction was allowed to cool to ambient temperature, water (100 ml) and chloroform (50 ml) were added. Layers were separated and the aqueous layer extracted further with chloroform (3×20 ml). Organics combined, washed with sat. brine (20 ml), dried (anh. Na$_2$SO$_4$) and the solvent evaporated to an off-white solid. The crude material was purified by a silica gel plug (eluent—chloroform then 5% MeOH/chloroform) this gave pure (R,R)-1,2-Bis[phenyl-(2-benzyloxy-phenyl)phosphine oxide]ethane (5.37 g, 96%).

Step 3—(R,R)-1,2-Bis[phenyl-(2-benzyloxy-phenyl) phosphino]ethane

To a solution of pure (R,R)-1,2-Bis[phenyl-(2-benzyloxy-phenyl)phosphine oxide]ethane (3.3 g, 5.13 mmol) and tributylamine (12.5 ml, 52.5 mmol) in acetonitrile (20 ml) under nitrogen gas at 70° C. was added trichlorosilane (4.7 ml, 46.5 mmol) dropwise over ~10 mins. After 3 hrs heating at 70° C. the reaction was allowed to cool to ambient temperature. The solution was added dropwise to ice cold 25% w/v NaOH (aq, 30 ml). Chloroform (50 ml) was added and the layers stirred and separated. The aqueous layer was extracted further with chloroform (2×20 ml). Organics were combined and evaporated to give a suspension in amine. The tributylamine layer was carefully decanted off and the resulting solid washed with heptane (3×20 ml). The solid was purified by flash column chromatography on silica gel (eluent–30% DCM in toluene+2% AcOH) this gave pure (R,R)-1,2-Bis[phenyl-(2-benzyloxy-phenyl)phosphino]ethane (2.5 g, 70%).

Step 4—(R,R)-1,2-Bis[boranato-phenyl-(2-benzyloxy-phenyl)phosphino]ethane

To a solution of (R,R)-1,2-Bis[phenyl-(2-benzyloxy-phenyl)phosphino]ethane (2.96 g, 4.85 mmol) in dry THF (20 ml) at ambient temperature was added BH$_3$.THF complex (1M in THF, 20 ml, 20 mmol) dropwise over ~20 mins. After 30 mins the reaction was worked up by the addition of water (50 ml) then 2M HCl (50 ml). Chloroform (80 ml) was added and the layers shaken and separated. The aqueous layer was extracted further with chloroform (2×50 ml). Organics were combined, washed with sat. brine (50 ml), dried (anh. Na$_2$SO$_4$), filtered and the solvent evaporated to give an off-white solid. The solid was purified by recrystallisation using toluene/heptane, this gave pure (R,R)-1,2-Bis[boranto-phenyl-(2-benzyloxy-phenyl)phosphino]ethane (2.18 g, 70%). $^1$H NMR (CDCl$_3$, 300 MHz): δ/ppm, 7.95 (2H, Ar—H, dd J=6.2, 13.5 Hz), 7.48-6.79 (28H, Ar—H, m), 4.80 (4H, —CH$_2$—O—Ar, dd J=11.7, 38.4 Hz), 2.60 (4H, —CH$_2$—P, ap. br. s); $^{31}$P NMR (CDCl$_3$, 105 Hz, $^1$H decoupled): δ/ppm, 19.3 (br. m)

(S,S) ligand was synthesized in a similar manner.

EXAMPLE 3

(S,S)-1,2-Bis[phenyl-(2-biphenyl)phosphino]ethane

Step 1—1-Magnesiumbromide-2-biphenyl

To a suspension of oven dried magnesium turnings (1.36 g, 55.8 mmol) in dry diethylether (75 ml) was added 1-bromo-2-biphenyl (10.0 g, 43 mmol) dropwise over ~60 mins to maintain a steady reflux. Some initial heating of the suspension was required to begin the reaction. After the addition the reaction was heated to reflux and stirred for 2 hrs. On cooling to ambient temperature this gave a brown solution of the Grignard, which was used immediately in the next reaction after filtration to remove some residual magnesium particles.

Step 2—Phenyl-(2-biphenyl)-Methyl-phosphine

A freshly prepared solution of 1-magnesiumbromide-2-biphenyl (43 mmol) in diethylether (~75 ml) was added dropwise to phenyldichlorophosphine (5.8 ml, 43 mmol) in dry diethylether (100 ml) at −78° C. (acetone/dry ice bath) over a period of ~1 hr. The reaction was stirred for 1 hr further at −78° C. then MeMgCl (3.0M in THF, 21.4 ml, 64.4 mmol) was added dropwise over ~1 hr. The reaction was allowed to warm to ambient temperature and stirred for a further 1 hr. The resulting phosphine is air-stable and therefore the following workup was carried out in the open air.

The solution was cooled to ~8° C. internal temperature, ice bath cooling and water (200 ml) cautiously added to destroy excess MeMgCl. The layers were shaken and separated. The aqueous layer was extracted further with diethylether (100 ml). Organics combined, washed with sat. sodium bicarbonate (2×50 ml), brine (50 ml) dried (anh. Na$_2$SO$_4$), filtered and the solvent evaporated to give an oil. The crude phosphine was purified by flash column chromatography on silica gel (eluent—hexane/toluene—1:1), this gave pure phenyl-(2-biphenyl)-Methyl-phosphine as a colourless oil (6.7 g, 56%).

Step 3—(R)-phenyl-(2-biphenyl)-methyl-phosphine oxide

To a solution of phenyl-(2-biphenyl)-methyl-phosphine (4.6 g, 29.1 mmol) in ethanol (30 ml) at ~4° C., ice bath cooling, was added 25% w/v aqueous hydrogen peroxide solution (~4 ml) dropwise over 10 mins. The solution was stirred for a further 2 hrs. After this time chloroform (80 ml) and water (80 ml) were added. The layers were shaken and separated. The aqueous layer was extracted further with chloroform (50 ml). Organics were combined, dried (anh. Na$_2$SO$_4$), filtered and the solvent evaporated to give phenyl-(2-biphenyl)-methyl-phosphine oxide (4.8 g, ~100%) Separation of the enantiomers was achieved using a Shimadzu preparative HPLC apparatus with a Varian fraction collector model 701, AS-H Chiralpak DAIC 20345 preparative column (2 cm×25 cm), 8 ml/min flow rate, 230 nm UV detection, 80-20 pentane-EtOH mobile phase and 50 mg injections. Retention Times 14.8 min and 20.1 min for the enantiomers This procedure gave gram quantities of pure (R) & (S)-phenyl-(2-biphenyl)-methyl-phosphine oxide (ee>99%).

Step 4—(R,R)-1,2-Bis[phenyl-(2-biphenyl)phosphine oxide]ethane

To a solution of (R)-phenyl-(2-biphenyl)-methyl-phosphine oxide (1.0 g, 3.4 mmol) in dry THF (10 ml) at −78° C. (acetone/dry ice bath) under nitrogen gas was added s-BuLi (1.4M in cyclohexane, 3.5 ml, 4.8 mmol) dropwise over ~30 mins. After a further 1 hr stirring Cu(I)Cl (0.48 g, 4.8 mmol) was added in one portion. The suspension was stirred for 10 min then Cu(II)Cl$_2$ (0.65 g, 4.8 mmol) was added. After a further 2 hrs stirring at the reaction was allowed to warm to ambient temperature and stirred overnight. In the morning EtOAc (200 ml) and sat. ammonium hydroxide (100 ml) where added. The layers were shaken and separated. The organic layer was washed further with sat. ammonium hydroxide (3×100 ml) until no blue colouration in the aqueous layer was apparent. Organics washed with sat. brine (50 ml), dried (anh. Na$_2$SO$_4$), filtered and the solvent evaporated to give an off white solid. The solid was slurried in diethylether and filtered to give pure (R,R)-1,2-Bis[phenyl-(2-biphenyl)phosphine oxide]ethane (0.70 g, 70%, ee>99%).

Step 5—(S,S)-1,2-Bis[phenyl-(2-biphenyl)phosphino]ethane

To a solution of pure (R,R)-1,2-Bis[phenyl-(2-biphenyl) phosphine oxide]ethane (0.70 g, 1.2 mmol) and tributylamine (1.7 ml, 7.2 mmol) in toluene (10 ml) under nitrogen gas at 70° C. was added trichlorosilane (0.73 ml, 7.2 mmol) dropwise over ~10 mins. After 5 hrs heating at 70° C. the reaction was allowed to cool to ambient temperature. The solution was added dropwise to ice cold 20% w/v KOH (aq, 30 ml). Toluene (20 ml) was added and the layers stirred and separated. The aqueous layer was extracted further with toluene (2×10 ml). Organics were combined and evaporated to give an off-white solid which was purified by a silica plug (eluent—hexane/toluene—4:1). This gave pure (S,S)-1,2-Bis[phenyl-(2-biphenyl)phosphino]ethane (0.4 g, 60%, ee>99%). $^1$H NMR (CDCl$_3$, 300 MHz): δ/ppm, 7.37-7.09 (28H, Ar—H, m), 1.86-1.76 (4H, —CH$_2$—P, ap. br. m); $^{31}$P NMR (CDCl$_3$, 105 Hz, $^1$H decoupled): δ/ppm, −19.5(s)

(R,R) ligand synthesized in a similar manner.

EXAMPLE 4

[(R,R)-1,2-Bis[(3,5-dimethylphenyl)-(ortho-tolyl)phosphino]ethane-Rh(cod)]tetrafluoroborate

Step 1—Synthesis of chloro-bis(diethylamino)-phosphine

To a solution of phosphorous trichloride (26 ml; 0.298 mol) in dry diethylether (500 ml) at −78° C., acetone/CO$_2$ bath, under dry nitrogen gas atmosphere was added diethylamine (123.4 ml; 1.19 mol) dropwise via a pressure equalised dropping funnel over 2 hrs. A thick suspension formed, reaction allowed to warm to ambient temperature and stirred for an additional 2 hrs. After this time the suspension was filtered under dry nitrogen gas via an oven dried filter stick, washing with dry diethylether (3×100 ml). Filtrate was evaporated under high vacuum on the Schlenk line, using a cold-finger trap to condense solvent vapours, to give an oil. The oil was purified by distillation under reduced pressure to give the required product (b.p. 105° C. @ 10 mmHg; 49 g; 70% yield). $^1$H NMR (300 MHz, CDCl$_3$), δ/ppm; 1.08 (6H, t J=7.0, CH$_3$), 3.08 (4H, ap. br. d J=7.0, CH$_2$); $^{31}$P NMR (121 MHz, CDCl$_3$) δ/ppm; 159.9.

NOTE—product is very water sensitive and reacts explosively on contact with water.

Step 2—Synthesis of dichloro-o-tolyl phosphine

To a solution of chloro-bis(diethylamino)-phosphine (16 ml; 76.1 mmol) in dry THF (400 ml) at −78° C., acetone/CO$_2$ bath, under dry nitrogen gas was added o-TolylMgCl Grignard (1M in THF; 91.3 ml) dropwise via pressure equalised dropping funnel over 30 mins. After the addition the reaction was allowed to warm to ambient temperature and stirred for an additional 1 hr. The solvent was removed via rotary evaporation to give a sticky gum. The gum was taken up in dry diethylether (500 ml) and 2M HCl in diethylether (153 ml) added dropwise over 20 mins. A thick suspension formed which was stirred overnight at ambient temperature. The solid was filtered off through a pre-dried filter stick, washing with dry diethylether (3×100 ml). The filtrate was evaporated under high vaccum on the Schlenk line, using a cold-finger trap to condense solvent vapours, to give a yellow oil. The oil was purified by distillation under reduced pressure to give the required product (b.p. 175° C. @ 5 mmHg; 8.7 g; 60% yield). $^1$H NMR (300 MHz, CDCl$_3$), δ/ppm; 2.68 (3H, s, CH$_3$), 7.25 (1H, ap. t J=6.8, Ar—H), 7.43 (2H, dd J=6.8, 9.8, Ar—H), 8.10 (1H, ap. t J=6.8, Ar—H); $^{31}$P NMR (121 MHz, CDCl$_3$) δ/ppm; 164.6.

Step 3—Synthesis of 3.5-dimethylphenyl magnesiumbromide

To oven dried magnesium turnings (0.76 g; 31.1 mmol) was added dry THF (3 ml), followed by a solution of 1-bromo-3,5-dimethylbenzene (3.52 ml; 25.91 mmol) in dry THF (50 ml), initially slowly until vigorous reaction was seen. Some heating with a heat gun and a crystal of iodine was needed to start the reaction. Addition was continued to maintain a steady reflux. Reaction mixture was heated for a further 2 hrs at reflux. Then allowed to cool to ambient temperature and used immediately as a solution of the Grignard in THF.

Step 4—Synthesis of (3.5-dimethylphenyl)-(ortho-tolyl)-methyl phosphine

A solution of freshly prepared Grignard (step 3; ~0.5 M in THF; 25.91 mmol) was added dropwise via a pressure equalised dropping funnel to dichloro-o-tolyl-phosphine (3.82 ml; 25.91 mmol) at −78° C. in dry THF (100 ml), acetone/CO$_2$ bath, under dry nitrogen gas over 1 hr. Reaction allowed to warm to ambient temperature, stirred for 30 mins, then re-cooled to −78° C. Then MeMgCl (3M in THF, 10.4 ml) added dropwise over 20 mins. Reaction allowed to warm to ambient temperature overnight. After this time, degassed water (5 ml) was carefully added to destroy excess Grignard. Stirred for 20 mins at ambient temperature, then the solvent was removed in vacuo. Degassed water (120 ml), degassed half sat. brine (15 ml) and diethylether (120 ml) were added. The layers were shaken in a nitrogen purged separating funnel. Layers separated and aq. layer extracted further with degassed diethylether (80 ml). Organics combined, dried (anh. Na$_2$SO$_4$), filtered and the solvent evaporated in vacuo to give a yellow oil. The oil was purified by distillation under reduced pressure to give the required product as a colourless oil (b.p. 250° C. @ 10 mmHg; 5.0 g; 80% yield). $^1$H NMR (300 MHz, CDCl$_3$), δ/ppm; 2.34 (9H, s, Ar—CH$_3$), 2.50 (3H, s, P—CH$_3$), 7.37-7.00 (7H, m, Ar—H); $^{31}$P NMR (121 MHz, CDCl$_3$) δ/ppm; −35.7.

Step 5—Synthesis of (3,5-dimethylphenyl)-(ortho-tolyl)-methyl phosphine-borane To a solution of (3.5-dimethylphenyl)-(ortho-tolyl)-methyl phosphine (4.0 g; 16.51 mmol) in dry THF (100 ml) at ambient temperature under dry nitrogen gas was added 1M borane-THF complex (20 ml; 20 mmol) dropwise over 15 mins. Reaction stirred for 2 hrs further, then water (100 ml) was added carefully, rapid fizzing seen. Volatile components were removed in vacuo and diethylether (100 ml) was added. Layers shaken and separated. The aq. layer was extracted further with diethylether (80 ml). Organics combined, dried (anh. Na$_2$SO$_4$), filtered and the solvent evaporated to give an oil which slowly solidified on standing at ambient temperature (4.2 g; 100% yield). $^1$H NMR (300 MHz, CDCl$_3$), δ/ppm; 0.60-1.40 (3H, br. m, BH$_3$), 1.83 (3H, s, P—CH$_3$), 2.21 (3H, s, Ar—CH$_3$), 2.30 (6H, s, Ar—H), 7.09-7.67 (7H, m, Ar—H); $^{31}$P NMR (121 MHz, CDCl$_3$) δ/ppm; 23.5 (br. m).

Step 6—Synthesis of enantiomerically pure (3.5-dimethylphenyl)-(ortho-tolyl)-methyl phosphine-borane Racemic borane was subjected to Preparative HPLC using an AS-H preparative column, 240 nm UV detection, 8 ml/min flowrate, 98:2 heptane-ethanol eluent, timed slot detection, retention times—enantiomer 1=14.5 min, enantiomer 2=18.5 min. This gave 350 mg of each enantiomer, ee>98%. $^1$H NMR (300 MHz, CDCl$_3$), δ/ppm; 0.60-1.40 (3H, br. m, BH$_3$), 1.83 (3H, s, P—CH$_3$), 2.21 (3H, s, Ar—CH$_3$), 2.30 (6H, s, Ar—CH$_3$), 7.09-7.67 (7H, m, Ar—H); $^{31}$P NMR (121 MHz, CDCl$_3$) δ/ppm; 23.5 (br. m).

Step 7—Synthesis of (R,R)-1,2-Bis[boranato(3,5-dimethylphenyl-(ortho-tolyl)phosphine]ethane To (3.5-dimethylphenyl)-(ortho-tolyl)-methyl phosphine-borane (0.33 g; 1.29 mmol) was added dry toluene (10 ml). The resulting solution was evaporated in order to remove residual water by formation of a toluene azeotrope. The process was repeated again and the oil taken up in dry THF (15 ml) under dry nitrogen gas atmosphere and cooled to −78° C., acetone/CO$_2$ bath. A solution of sBuLi in hexanes (1.4 M, 1.82 ml) was added via syringe pump over 20 mins. The reaction was stirred for 1.5 hrs then Cu(I)Cl (128 mg; 1.29 mmol) was added in one portion. Reaction allowed to warm to ambient temperature. After 30 mins, Cu(II)Cl$_2$ (260 mg; 1.94 mmol) was added in one portion. Reaction stirred overnight at ambient temperature. After this time, 30wt % ammonia in water (20 ml) was added followed by EtOAc (40 ml). Layers shaken and separated. The aq. layer was extracted further with EtOAc (30 ml). Organics combined, washed with 10 wt % ammonia in water (3×40 ml), half sat. brine (40 ml), dried (anh. Na$_2$SO$_4$), filtered and the solvent evaporated to give an oil. The oil was purified by flash column chromatography on silica gel (eluent—toluene). Fractions containing pure product were pooled together to give an oil which solidified slowly on standing at ambient temperature. The solid was recrystallised from hot toluene/heptane (1:2) to give a crystalline solid (150 mg, 40% yield). $^1$H NMR (300 MHz, CDCl$_3$), δ/ppm; 0.60-1.40 (6H, br. m, BH$_3$), 2.15 (6H, s, Ar—CH$_3$), 2.28 (6H, s, Ar—CH$_3$), 2.35 (12H, s, Ar—CH$_3$), 2.40-2.50 (4H, m, P—CH$_2$—), 7.07-7.65 (14H, m, Ar—H); $^{31}$P NMR (121 MHz, CDCl$_3$) δ/ppm; 19.1 (br. m).

Step 8—Synthesis of [(R,R)-1,2-Bis[(3,5-dimethylphenyl-(ortho-tolyl)phosphino]ethane-Rh(cod)] tetrafluoroborate To (R,R)-1,2-Bis[boranato(3,5-dimethylphenyl-(ortho-tolyl)-phosphino]ethane (25 mg; 0.05 mmol) in a 10 ml Schlenk flask was added degassed diethylamine (2 ml). The reaction was heated to 45° C. internal temperature and stirred for 2 hrs under nitrogen gas. After this time, volatile components were removed under high vacuum and the residue taken up in degassed heptane (2 ml), insoluble salts were removed via filtration through a syringe filter, washing with degassed heptane (2×1 ml). Solvent removed under high vacuum and the residue taken up in degassed MeOH/EtOH (9:1, 2 ml), Rh(cod)Cl dimer (12.1 mg; 0.025 mmol) was added under a positive pressure of nitrogen gas. The resulting bright red solution was stirred for 1 hr at ambient temperature. After this time degassed sodium tetrafluoroborate solution (1.2 M in water, 0.06 ml; 0.075 mmol) was added dropwise over 2 mins via a microsyringe. The resulting solid was stirred for 30 mins, then the solvent was removed in vacuo and degassed MeOH added (2×2 ml) to azeotrope off residual water. The solid was taken up in degassed dichloromethane (2 ml), filtered through a syringe filter, washing with degassed DCM (2×1 ml). Solvent removed in vacua to give a bright red solid, which was used crude without further purification (~20 mg). The catalyst was used immediately for hydrogenation studies using a multi-well Argonaut Endeavour hydrogenator.

Example 5

Synthesis of [(R,R)-1,2-Bis[(4-methoxy-2,3,5-trimethylphenyl-phenylphosphino]ethane-Rh(cod)]tetrafluoroborate Step 1—Synthesis of 4-bromo-2,3,6-trimethyl phenol To a solution of 2,3,6-trimethylphenol (40 g; 0.294 mol) in DCM (600 ml) at ambient temperature was added a solution of bromine (16.6 ml; 0.294 mol) in DCM (300 ml) dropwise over 30 mins. Reaction stirred for a further 5 hrs at ambient temperature. A solution of 1M sodium sulfite (300 ml) was added. The layers were separated and the aq. layer extracted with DCM (150 ml). Organics combined, washed with half sat. brine (300 ml), dried (anh. MgSO$_4$), filtered and the solvent evaporated to give a white solid (66.2 g; 105% Th.). $^1$H NMR (300 MHz, CDCl$_3$), δ/ppm; 2.19 (3H, s, Ar—CH$_3$), 2.22 (3H, s, Ar—CH$_3$), 2.34 (3H, s, Ar—CH$_3$), 7.18 (1H, s, Ar—H).

Step 2—Synthesis of 1-bromo-4-methoxy-2,3,5-trimethyl-benzene

To a solution of 4-bromo-2,3,6-trimethyl phenol (66.2 g; 0.294 mol) in acetone (2 L) was added potassium carbonate (203 g; 1.47 mol) at ambient temperature. Then MeI (91.4 ml; 1.47 mol) was added dropwise over 30 mins. Reaction was stirred overnight at ambient temperature. After this time the mixture was filtered, washing with acetone (2×200 ml) and the filtrate evaporated to give a red solid. The solid was taken up in DCM (1.2 L) and washed with 1M sodium thiosulfate (2×400 ml), half sat. brine (800 ml), dried (anh. MgSO$_4$), filtered and the solvent evaporated to give a red oil (53.8 g; 80%). $^1$H NMR (300 MHz, CDCl$_3$), δ/ppm; 2.23 (3H, s, Ar—CH$_3$), 2.25 (3H, s, Ar—CH$_3$), 2.32 (3H, s, Ar—CH$_3$), 3.66 (3H, s, Ar—OCH$_3$), 7.23 (1H, s, Ar—H).

Step 3—Synthesis of (4-methoxy-2,3,5-trimethylphenyl)-phenyl-methyl phosphine borane To a solution of 1-bromo-4-methoxy-2,3,5-trimethyl-benzene (5.02 g; 21.91 mmol) in dry THF (80 ml) at −78° C., acetone/CO$_2$ bath, under dry nitrogen gas was added nBuLi (1.6M in hexanes, 16.4 ml) dropwise over 10 mins. The reaction was stirred for a further 30 mins, then added via cannula to a −78° C. solution of dichlorophenyl phosphine (2.97 ml; 21.91 mmol) in dry THF (100 ml) over ~10 mins. Reaction stirred for 1 hr then allowed to warm to ambient temperature and stirred for an additional 3 hrs. Reaction re-cooled to −78° C. and MeMgCl (3M in THF, 8.8 ml) was added over 5 mins. The newly formed suspension was stirred overnight at ambient temperature. After this time 1M borane-THF complex (25 ml; 25 mmol) was added dropwise over 10 mins. Reaction stirred for 2 hrs then water (100 ml) was slowly added followed by chloroform (150 ml). Layers shaken and separated. The aq. layer was extracted further with chloroform (100 ml). Organics combined, washed with half sat. brine (100 ml), dried (anh. MgSO$_4$), filtered and the solvent evaporated to give an oil. The oil was purified by flash column chromatography on silica gel (eluent—toluene) to give a white solid (1.8 g; 29%). $^1$H NMR (300 MHz, CDCl$_3$), δ/ppm; 0.50-1.15 (3H, br. m, BH$_3$), 1.82 (3H, ap. d J=9.8, P—CH$_3$), 2.06 (3H, s, Ar—CH$_3$), 2.15 (3H, s, Ar—CH$_3$), 2.35 (3H, s, Ar—CH$_3$), 3.71 (3H, s, Ar—OCH$_3$), 7.15-7.60 (6H, m, Ar—H). $^{31}$P NMR (121 MHz, CDCl$_3$) δ/ppm; 11.2 (br. m).

Step 4—Synthesis of Enantiomerically Pure (4-methoxy-2,3,5-trimethylphenyl)-phenyl-methyl phosphine borane Racemic borane was subjected to Preparative HPLC using an (S,S)-Whelk-01 preparative column, 260 nm UV detection, 10 ml/min flowrate, 98:2 heptane-ethanol eluent, timed slot detection, retention times—enantiomer 1=21.5 min, enantiomer 2=25.0 min. This gave 300 mg of each enantiomer, ee=92% for enantiomer 1 and ee=80% for enantiomer 2. $^1$H NMR (300 MHz, CDCl$_3$), δ/ppm; 0.50-1.15 (3H, br. m, BH$_3$), 1.82 (3H, ap. d J=9.8, P—CH$_3$), 2.06 (3H, s, Ar—CH$_3$), 2.15 (3H, s, Ar—CH$_3$), 2.35 (3H, s, Ar—CH$_3$), 3.71 (3H, s, Ar—OCH$_3$), 7.15-7.60 (6H, m, Ar—H). $^{31}$P NMR (121 MHz, CDCl$_3$) δ/ppm; 11.2 (br. m).

Step 5—Synthesis of (S,S)-1,2-Bis[boranato(4-methoxy-2,3,5-trimethylphenyl)-phenyl phosphino]ethane To a solution of (4-methoxy-2,3,5-trimethylphenyl)-phenyl-methyl phosphine borane (280 mg; 0.98 mmol) in dry THF (20 ml) at −78° C., acetone/CO$_2$ bath, under dry nitrogen gas was added sBuLi (0.85M in hexanes, 1.38 ml) via syringe pump over 30 mins. The solution was stirred for a further 2 hrs and then Cu(I)Cl (97 mg; 0.98 mmol) was added in one portion. Reaction allowed to warm to ambient temperature and stirred for a further 30 mins, then Cu(II)Cl$_2$ (158 mg; 1.18 mmol) was added in one portion. Reaction was stirred overnight at ambient temperature. After this time 15 wt % of ammonia in water (20 ml) and EtOAc (20 ml) were added. Layers shaken and separated. The aq. layer was extracted further with EtOAc (20 ml). Organics combined, washed with 15 wt % ammonia in water (4×30 ml), half sat. brine (30 ml), dried (anh. MgSO$_4$), filtered and the solvent evaporated to give an oil. The oil was purified by flash column chromatography on silica gel (eluent—toluene) to give a solid. The solid was recrystallised from hot toluene/n-hexane (1:2) to give pure product (60 mg; 22%). $^1$H NMR (300 MHz, CDCl$_3$), δ/ppm; 0.50-1.20 (6H, br. m, BH$_3$), 2.00 (6H, s, Ar—CH$_3$), 2.05 (4H, m, P—CH$_2$—), 2.13 (6H, s, Ar—CH$_3$), 2.31 (6H, s, Ar—CH$_3$), 3.71 (6H, s, Ar—OCH$_3$), 7.15-7.52 (12H, m, Ar—H). $^{31}$P NMR (121 MHz, CDCl$_3$) δ/ppm; 19.1 (br. m).

Step 8—Synthesis of [(S,S)-1,2-Bis[(4-methoxy-2,3,5-trimethylphenyl-phenyl phosphino]ethane-Rh(cod)]tetrafluoroborate To (S,S)-1,2-Bis[boranato(4-methoxy-2,3,5-trimethylphenyl-phenyl phosphino]ethane (15 mg; 0.026 mmol) in a 10 ml Schlenk flask was added degassed diethylamine (2 ml). The reaction was heated to 45° C. internal temperature and stirred for 2 hrs under nitrogen gas. After this time, volatile components were removed under high vacuum and the residue taken up in degassed heptane (2 ml), insoluble salts were removed via filtration through a syringe filter, washing with degassed heptane (2×1 ml). Solvent removed under high vacuum and the residue taken up in degassed MeOH/EtOH (9:1, 1.5 ml), Rh(cod)Cl dimer (6.5 mg; 0.013 mmol) was added under a positive pressure of nitrogen gas. The resulting bright red solution was stirred for 1 hr at ambient temperature. After this time degassed sodium tetrafluoroborate solution (1.2 M in water, 0.04 ml; 0.039 mmol) was added dropwise over 2 mins via a microsyringe. The resulting solid was stirred for 30 mins, then the solvent was removed in vacuo and degassed MeOH added (2×2 ml) to azeotrope off residual water. The solid was taken up in degassed dichloromethane (2 ml), filtered through a syringe filter, washing with degassed DCM (2×1 ml). Solvent removed in vacuo to give a bright red/orange solid, which was used crude without further purification (~20 mg). The catalyst was used immediately for hydrogenation studies using a multi-well Argonaut Endeavour hydrogenator.

EXAMPLE 6

Synthesis of [(R,R)-1,2-Bis[(3,5-dimethylphenyl-phenyl-phosphino]-ethane-Rh(cod)]tetrafluoroborate

Step 1—Synthesis of (2-methoxy-3,5-dimethyl-phenyl)-phenyl-methyl-phosphine-borane To a solution of 12.5 g (47.7 mmol) 1-Iodo-2-methoxy-3,5-dimethylbenzene in 150 ml dry THF are added under a nitrogen atmosphere 47.7 ml of a 1.0 M solution of isopropylmagnesiumchloride.LiCl in THF at −78° C. The Grignard solution is allowed to warm to room temperature (2 h) and then added via a dropping funnel to a cooled (−78° C.) solution of 8.1 g (45 mmol) PhPCl$_2$ in 100 ml dry THF over a period of ca. 1 h. The solution is allowed to warm to room temperature and stirred for 3 h (a colour change to orange is observed during this time). The reaction mixture is then treated with 20 ml of a 3.0 M solution of MeMgCl in THF (60 mmol) and stirred at room temperature for 1 h (orange colour disappears). Borane-THF complex (1.0 M in THF, 75 ml) is then added and the solution left stirring overnight. The reaction is then carefully quenched with water (100 ml), the organic layer separated and the aqueous layer extracted with CH$_2$Cl$_2$ (2×100 ml). The combined organic layers are washed with brine (2×200 ml), dried over Na$_2$SO$_4$, filtered and evaporated to dryness in vacuo. The oily crude product is purified on a silica column (30×5 cm, eluent cyclohexane: EtOAc—4:1) to yield 3.6 g (13.2 mmol, 29%) of pure racemic product.
$^1$H-NMR (500 MHz, CDCl$_3$), δ (ppm)=7.5-6.9 (m, 7H, Ar—H), 3.85 (s, 3H, —OCH$_3$), 2.21 (s, 3H, Ar—CH$_3$), 2.07 (s, 3H, Ar—CH$_3$), 1.88 (d, 3H, P—CH$_3$), 1.3-0.7 (br, m, 3H, BH$_3$). —$^{31}$P-NMR (243 MHz, CDCl$_3$), δ (ppm)=10.9 (m).

Step 2—Enantiomerically Pure (2-Methoxy-3,5-dimethyl-phenyl)-phenyl-methyl-phosphine-borane Racemic borane was subjected to preparative HPLC using a Daicel Chiralpak ASH preparative column (25 cm×2 cm), 210 nm UV detection, 4 ml/min flowrate, 70:30 heptane-ethanol eluent, timed slot detection, retention times—enantiomer 1=19.75 min, enantiomer 2=25.5 min. This gave ca. 350 mg of each enantiomer, ee=95% for enantiomer 1 (probably (R)-configuration) and ee=90% for enantiomer 2 (probably (S)-configuration).

Step 3—Synthesis of (R,R)-1,2-Bis[boranato(2-methoxy-3,5-dimethyl-phenyl)-phenyl-phosphino]ethane A sample (266 mg, 0.98 mmol) of (R)-(2-methoxy-3,5-dimethyl-phenyl)-phenyl-methyl-phosphine-borane is dissolved in 5 ml dry THF under a nitrogen atmosphere and then the solvent evaporated in vacuo. The process is repeated one more time to azeotropically remove residual moisture from the sample. The dried material is then dissolved in 15 ml THF and cooled to −78° C. A solution of n-BuLi (1.6 M, 0.75 ml, 1.2 mmol) is slowly added via syringe pump over a period of 30 minutes. After stirring for 2 h at −78° C., anhydrous copper(II) chloride (161 mg, 1.2 mmol) is added. A colour change to green is observed and the mixture is kept at room temperature over night. Then 25 ml of an aqueous $NH_3$ solution (25%) are added, the organic layer is separated and the aqueous layer extracted with 2×25 ml $CH_2Cl_2$. The combined organic layers are washed with brine (2×25 ml) until the blue colour of the copper-ammonia complex is no longer observed, dried over sodium sulphate and filtered. After removal of the solvent in vacuo, a crude oily residue (250 mg) remains which is purified by column chromatography (silica 40×5 cm, eluent toluene), yielding 42 mg (0.08 mmol, 16%) pure product as a white solid).

$^1$H-NMR (500 MHz, $CDCl_3$), δ(ppm)=7.5-6.9 (m, 14H, Ar—H), 3.85 (s, 6H, —$OCH_3$), 2.44 (m, 4H, P—$CH_2$—), 2.23 (s, 6H, Ar—$CH_3$), 2.00 (s, 6H, Ar—$CH_3$), 1.2-0.6(m, br, 6H, $BH_3$). —$^{31}$P-NMR (243 MHz, $CDCl_3$), δ (ppm)=19.5 (m).

Step 4—Synthesis of [(R,R)-1,2-Bis[(3,5-dimethylphenyl-phenyl-phosphino]ethane-Rh(cod)]tetrafluoroborate

[(R,R)-1,2-Bis[(3,5-dimethylphenyl-phenylphosphino]ethane (21 mg, 0.04 mmol) is dissolved in 2 ml degassed diethylamine and heated to 45° C. for 2 h (TLC indicates formation of free phosphine). Volatiles are then removed in vacuo and the residue is redissolved in 2 ml n-heptane. Insoluble material is removed by filtration through a syringe filter. The solution is evaporated to dryness and the remaining white solid then taken up in 2 ml of a degassed Methanol/Ethanol mixture (9:1) to form a suspension. Then [Rh(COD)Cl]$_2$ (9.7 mg, 0.02 mmol) are added and the mixture is stirred for 1 h at room temperature. The solution takes on a bright orange colour. Sodium tetrafluoroborate solution (1.2 M in water, 50 μL, 0.06 mmol) is then added. The mixture is stirred for 30 min at room temperature and the formation of an orange-red precipitate is observed. All volatiles are removed in vacuo, the remaining residue azeotroped with methanol (2×3 ml) to remove water and the dry residue then redissolved in $CH_2Cl_2$. After filtration through a syringe filter, the solution is evaporated to dryness to yield 25 mg of a dark red solid that is used without further purification as a hydrogenation catalyst.

EXAMPLE 7

[Ru{(S,S)-1,2-bis(phenyl-(2-biphenyl)phosphino)ethane}Cl$_2$]

(S,S)-1,2-Bis[phenyl-(2-biphenyl)phosphino]ethane (11.5 mg, 0.025 mmol) and [Ru(cod)bis(methylallyl)] (6.4 mg, 0.020 mmol) were placed in a Schlenk tube under a nitrogen atmosphere. Nitrogen-purged toluene (1 mL) was added and the mixture heated in a 70° C. oil bath for 5 h, then allowed to cool to room temperature. $^{31}$P NMR analysis of a small sample ($CDCl_3$, 105 Hz, $^1$H decoupled) showed a peak at 90.3 ppm, attributed to the Ru-bisphosphine complex. The mixture was then treated with an ethereal solution of HCl (1.0M, 55 μL, 0.055 mmol), whereupon a colour change from red to orange was immediately observed. The mixture was stirred for a further 2 h, concentrated to dryness, and used immediately and without purification.

EXAMPLE 8

[Rh{(S,S)-1,2-bis(phenyl-(2-biphenyl)phosphino)ethane}{cod}]BF$_4$ (S,S)-1,2-Bis[phenyl-(2-biphenyl)phosphino]ethane (30 mg, 0.055 mmol) and [Rh(cod)Cl]$_2$ (12 mg, 0.025 mmol) were placed in a Schlenk tube under a nitrogen atmosphere. A nitrogen-purged methanol-ethanol mixture (9:1, 2 mL) was added and the mixture stirred at room temperature for 2 h. An aqueous solution of NaBF$_4$ (1.2M, 100 μL, 0.12 mmol) was added, and stirring continued for a further 1 h. The solvent was removed under high vacuum, and the residue stripped with further solvent (2 mL). $^{31}$P NMR analysis of a small sample ($CDCl_3$, 105 Hz, $^1$H decoupled) showed a doublet (J=148 Hz) at 58.0 ppm, attributed to the Rh-bisphosphine complex. Finally, the residue was taken up in nitrogen-purged $CH_2Cl_2$, filtered using a PTFE syringe filter and concentrated once more, affording an orange solid that was used immediately and without further purification.

EXAMPLE 9

Comparison of Compounds of General Formula II and III with DiPAMP in Organic Synthesis Rh-phosphine complexes were prepared by procedures similar to that in Example 8. Hydrogenations were performed in an Argonaut Endeavour multi-well hydrogenator with computer-controlled hydrogen uptake monitoring. Freshly prepared catalyst (loading indicated in table) and substrate (200 mg) were weighed into an individual oven-dried Argonaut glass liner in the air, except for low catalyst loading experiments (i.e. 1000:1-20000:1) where a standard solution of the catalyst in degassed MeOH (0.5 mg/mL) was added via the injection port. The liners were placed in the Argonaut wells and the equipment assembled. Each well was purged with nitrogen gas (3×100 psi) and degassed MeOH (2 mL) was added via the injection port. Each well was purged with nitrogen gas (3×100 psi) and heated to the required temperature. The Argonaut program used the following standard conditions; 400 rpm rotation speed, 150 psi hydrogen pressure and 10 h run time.

Figure 1: Ligands used in this study

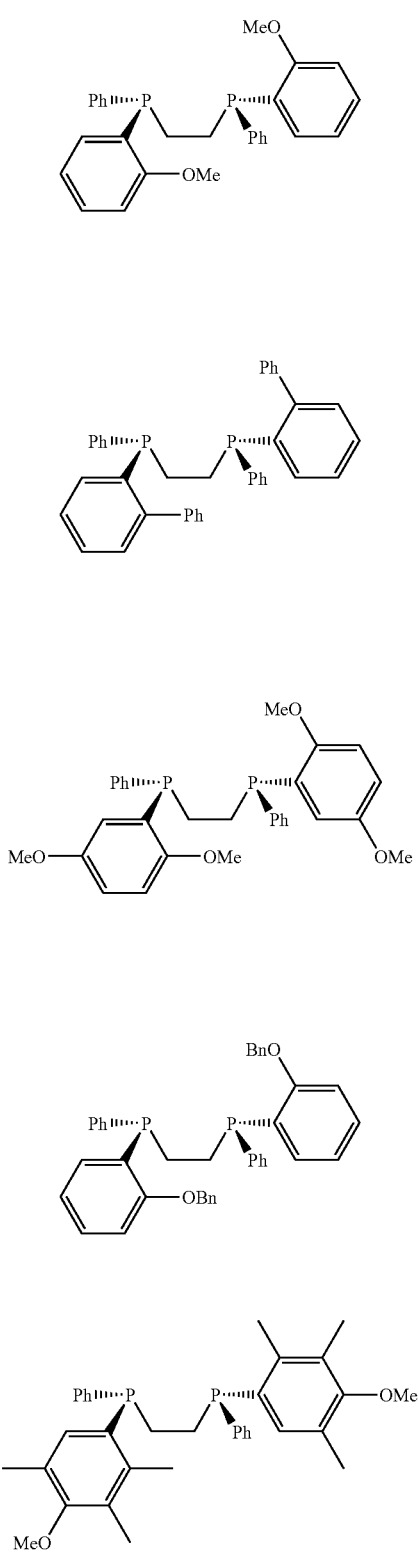

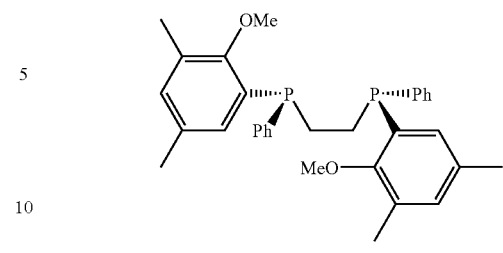

TABLE 1

Asymmetric Hydrogenation using chiral bisphosphines

| #[a] | L* | R | Temp °C. | Loading | % conversion | % ee[b] |
|---|---|---|---|---|---|---|
| 1 | 1 | Me | 50 | 200:1 | 100 | 93 |
| 2 | 2 | Me | 30 | 200:1 | 100 | >99 |
| 3 | 4 | Me | 20 | 250:1 | 100 | 96 |
| 4 | 1 | H | 50 | 200:1 | 100 | 91 |
| 5 | 2 | H | 30 | 200:1 | 100 | >99 |

[a]Standard reactions conditions to form catalysts and standard hydrogenation conditions;
[b]ee determined by HPLC analysis

TABLE 2

Hydrogenation with various substrates

| #[a] | L*[b] | R[1] | R[2] | Temp °C. | % ee[c] |
|---|---|---|---|---|---|
| 1 | 1 | 2-naphthyl | H | 50 | 89 |
| 2 | 2 | 2-naphthyl | H | 30 | >99 |
| 3 | 3 | 2-naphthyl | H | 50 | 92 |
| 4 | 1 | 4-chlorophenyl | Me | 50 | 92 |
| 5 | 2 | 4-chlorophenyl | Me | 30 | >99 |
| 6 | 6 | 4-chlorophenyl | Me | 50 | 96 |
| 7 | 1 | 4-chlorophenyl | H | 50 | 88 |
| 8 | 2 | 4-chlorophenyl | H | 30 | >99 |
| 9 | 1 | H | Me | 50 | 92 |
| 10 | 2 | H | Me | 30 | >99 |

[a]All conversions were quantitative using standard catalyst formation and hydrogenation conditions;
[b]Substrate:ligand ratio 200:1;
[c]ee determined by HPLC analysis

TABLE 3

Hydrogenation with a pyridinium substrate

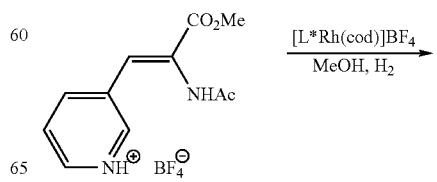

TABLE 3-continued

[Structure: CO2Me, NHAc, NH+ BF4- substrate]

| #[a] | L*[b] | Temp °C. | % conversion | % ee[c] |
|---|---|---|---|---|
| 1 | 1 | 50 | 100 | 91 |
| 2 | 2 | 30 | 100 | 97 |
| 3 | 5 | 22 | 100 | 99 |
| 4 | 6 | 50 | 100 | 99 |

[a] Standard reactions conditions to form catalysts and standard hydrogenation conditions;
[b] Substrate:ligand ratio 200:1;
[c] ee determined by HPLC analysis

TABLE 4

Hydrogenation of an enol acetate

[Reaction scheme: Ph-C(=CH2)-OAc → Ph-CH*-OAc, [L*Rh(cod)]BF4, MeOH, H2]

| #[a] | L*[b] | Temp °C. | % conversion | % ee[c] |
|---|---|---|---|---|
| 1 | 1 | 50 | 100 | 57 |
| 2 | 2 | 30 | 100 | 96 |
| 3 | 3 | 50 | 100 | 63 |
| 4 | 6 | 50 | 100 | 80 |

[a] Standard reactions conditions to form catalysts and standard hydrogenation conditions using;
[b] Substrate:Ligand ratio 200:1;
[c] ee determined by HPLC analysis All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

REFERENCES

Ojima, I., Ed., Catalytic Asymmetric Synthesis; 2nd. Edn., Wiley-VCH, 2000
Knowles, W. S. *J. Chem. Ed.*, 1986, 63, 222
Kagan, H. B. *Bull. Chim. Soc. Fr.*, 1988, 846
Noyori, R. *Chem. Soc. Rev.*, 1989, 18, 187

The invention claimed is:

1. A P-chiral compound of general formula (II):

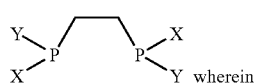

(II)

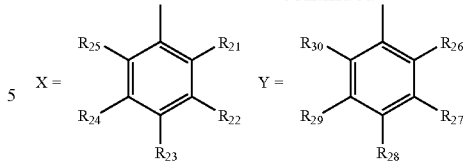

wherein at least one of $R_{21}$, $R_{25}$, $R_{26}$ and $R_{30}$ is independently selected from $C_{1-4}$ alkyl, $CF_3$, phenyl and benzyloxy and the remaining substituents selected from $R_{21}$, $R_{25}$, $R_{26}$ and $R_{30}$ are hydrogen; at least one of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen; and $R_{23}$ and $R_{28}$ are independently selected from hydrogen, $C_{1-4}$ alkyl, $CF_3$, $C_{1-4}$ alkoxy, phenyl and benzyloxy.

2. A P-chiral compound of claim 1 wherein, $R_{21}$, $R_{25}$, $R_{26}$ and $R_{30}$ are independently selected from $C_{1-4}$ alkyl, $CF_3$, phenyl and benzyloxy; and $R_{22}$, $R_{24}$, $R_{27}$ and $R_{29}$ are independently selected from $C_{1-4}$ alkyl, $CF_3$, $C_{1-4}$ alkoxy, phenyl and benzyloxy.

3. A P-chiral compound of claim 1 wherein, $R_{21}$, $R_{25}$, $R_{26}$ and $R_{30}$ are independently selected from $C_{1-4}$ alkyl, $CF_3$, phenyl and benzyloxy; and three of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituent selected from $R_{22}$, $R_{24}$, $R_{27}$ and $R_{29}$ is hydrogen.

4. A P-chiral compound of claim 1 wherein, $R_{21}$, $R_{25}$, $R_{26}$ and $R_{30}$ are independently selected from $C_{1-4}$ alkyl, $CF_3$, phenyl and benzyloxy; and two of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

5. A P-chiral compound of claim 1 wherein, $R_{21}$, $R_{25}$, $R_{26}$ and $R_{30}$ are independently selected from $C_{1-4}$ alkyl, $CF_3$, phenyl and benzyloxy; and one of $R_{22}$, $R_{24}$, $R_{27}$ and $R_{29}$ is independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

6. A P-chiral compound of claim 1 wherein, three of $R_{21}$, $R_{25}$, $R_{26}$ and $R_{30}$ are independently selected from $C_{1-4}$ alkyl, $CF_3$, phenyl and benzyloxy and the remaining substituent selected from $R_{21}$, $R_{25}$, $R_{26}$ and $R_{30}$ is hydrogen; and $R_{22}$, $R_{24}$, $R_{27}$ and $R_{29}$ are independently selected from $C_{1-4}$ alkyl, $CF_3$, $C_{1-4}$ alkoxy, phenyl and benzyloxy.

7. A P-chiral compound of claim 1 wherein, three of $R_{21}$, $R_{25}$, $R_{26}$ and $R_{30}$ are independently selected from $C_{1-4}$ alkyl, $CF_3$, phenyl and benzyloxy and the remaining substituent selected from $R_{21}$, $R_{25}$, $R_{26}$ and $R_{30}$ is hydrogen; and three of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituent selected from $R_{22}$, $R_{24}$, $R_{27}$ and $R_{29}$ is hydrogen.

8. A P-chiral compound of claim 1 wherein, three of $R_{21}$, $R_{25}$, $R_{26}$ and $R_{30}$ are independently selected from $C_{1-4}$ alkyl, $CF_3$, phenyl and benzyloxy and the remaining substituent selected from $R_{21}$, $R_{25}$, $R_{26}$ and $R_{30}$ is hydrogen; and two of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

9. A P-chiral compound of claim 1 wherein, three of $R_{21}$, $R_{25}$, $R_{26}$ and $R_{30}$ are independently selected from $C_{1-4}$ alkyl, $CF_3$, phenyl and benzyloxy and the remaining substituent selected from $R_{21}$, $R_{25}$, $R_{26}$ and $R_{30}$ is hydrogen; and one of $R_{22}$, $R_{24}$, $R_{27}$ and $R_{29}$ is independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

10. A P-chiral compound of claim 1 wherein, two of $R_{21}$, $R_{25}$, $R_{26}$ and $R_{30}$ are independently selected from $C_{1-4}$ alkyl, $CF_3$, phenyl and benzyloxy and the remaining substituents selected from $R_{21}$, $R_{25}$, $R_{26}$ and $R_{30}$ are hydrogen; and $R_{22}$, $R_{24}$, $R_{27}$ and $R_{29}$ are independently selected from $C_{1-4}$ alkyl, $CF_3$, $C_{1-4}$ alkoxy, phenyl and benzyloxy.

11. A P-chiral compound of claim 1 wherein, two of $R_{21}$, $R_{25}$, $R_{26}$ and $R_{30}$ are independently selected from $C_{1-4}$ alkyl, $CF_3$, phenyl and benzyloxy and the remaining substituents selected from $R_{21}$, $R_{25}$, $R_{26}$ and $R_{30}$ are hydrogen; and three of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituent selected from $R_{22}$, $R_{24}$, $R_{27}$ and $R_{29}$ is hydrogen.

12. A P-chiral compound of claim 1 wherein, two of $R_{21}$, $R_{25}$, $R_{26}$ and $R_{30}$ are independently selected from $C_{1-4}$ alkyl, $CF_3$, phenyl and benzyloxy and the remaining substituents selected from $R_{21}$, $R_{25}$, $R_{26}$ and $R_{30}$ are hydrogen; and two of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

13. A P-chiral compound of claim 1 wherein, two of $R_{21}$, $R_{25}$, $R_{26}$ and $R_{30}$ are independently selected from $C_{1-4}$ alkyl, $CF_3$, phenyl and benzyloxy and the remaining substituents selected from $R_{21}$, $R_{25}$, $R_{26}$ and $R_{30}$ are hydrogen; and one of $R_{22}$, $R_{24}$, $R_{27}$ and $R_{29}$ is independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

14. A P-chiral compound of claim 1 wherein, one of $R_{21}$, $R_{25}$, $R_{26}$ and $R_{30}$ are independently selected from $C_{1-4}$ alkyl, $CF_3$, phenyl and benzyloxy and the remaining substituents selected from $R_{21}$, $R_{25}$, $R_{26}$ and $R_{30}$ are hydrogen; and $R_{22}$, $R_{24}$, $R_{27}$ and $R_{29}$ are independently selected from $C_{1-4}$ alkyl, $CF_3$, $C_{1-4}$ alkoxy, phenyl and benzyloxy.

15. A P-chiral compound of claim 1 wherein, one of $R_{21}$, $R_{25}$, $R_{26}$ and $R_{30}$ are independently selected from $C_{1-4}$ alkyl, $CF_3$, phenyl and benzyloxy and the remaining substituents selected from $R_{21}$, $R_{25}$, $R_{26}$ and $R_{30}$ are hydrogen; and three of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituent selected from $R_{22}$, $R_{24}$, $R_{27}$ and $R_{29}$ is hydrogen.

16. A P-chiral compound of claim 1 wherein, one of $R_{21}$, $R_{25}$, $R_{26}$ and $R_{30}$ are independently selected from $C_{1-4}$ alkyl, $CF_3$, phenyl and benzyloxy and the remaining substituents selected from $R_{21}$, $R_{25}$, $R_{26}$ and $R_{30}$ are hydrogen; and two of $R_{22}$, $R_{24}$, $R_{27}$ and $R_{29}$ are independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

17. A P-chiral compound of claim 1 wherein, one of $R_{21}$, $R_{25}$, $R_{26}$ and $R_{30}$ are independently selected from $C_{1-4}$ alkyl, $CF_3$, phenyl and benzyloxy and the remaining substituents selected from $R_{21}$, $R_{25}$, $R_{26}$ and $R_{30}$ are hydrogen; and one of $R_{22}$, $R_{24}$, $R_{27}$ and $R_{29}$ is independently selected from $C_{1-4}$ alkyl, $CF_3$, $C_{1-4}$ alkoxy, phenyl and benzyloxy and the remaining substituents selected from $R_{22}$, $R_{24}$, $R_{27}$ and $R_{29}$ are hydrogen.

18. A P-chiral compound of general formula (III):

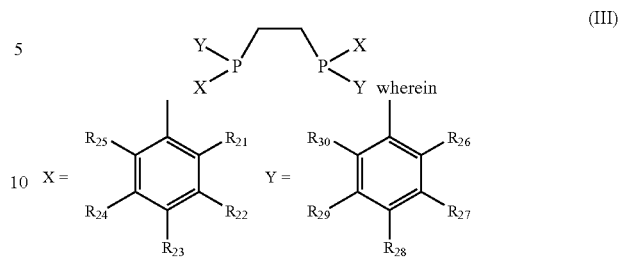

wherein at least one of $R_{21}$, $R_{25}$, $R_{26}$ and $R_{30}$ is independently selected from phenyl and benzyloxy and the remaining substituents selected from $R_{21}$, $R_{25}$, $R_{26}$ and $R_{30}$ are hydrogen; and $R_{22}$, $R_{23}$, $R_{24}$, $R_{27}$, $R_{28}$ and $R_{29}$ are independently selected from hydrogen, $C_{1-4}$ alkyl, $CF_3$, $C_{1-4}$ alkoxy, phenyl and benzyloxy.

19. A process for the preparation of a P-chiral compound of general formula (II) or general formula (III) as defined in claim 1 or claim 18, respectively, which comprises reducing a P-chiral compound of formula (XII):

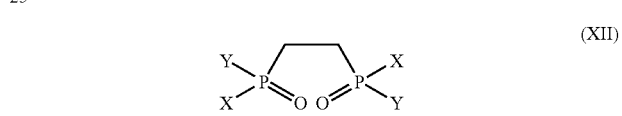

20. A process for the preparation of a P-chiral compound of general formula (II) or general formula (III) as defined in claim 1 or claim 18, respectively, which comprises reducing a P-chiral compound of formula (XIII):

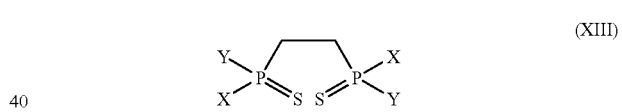

21. A process for the preparation of a P-chiral compound of general formula (II) or general formula (III) as defined in claim 1 or claim 18, respectively, which comprises deboronating a P-chiral compound of formula (XIV):

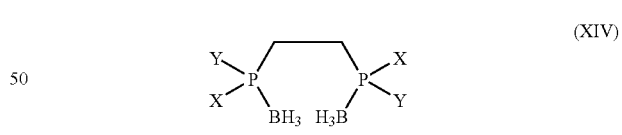

22. A transition metal complex comprising a P-chiral compound of claim 18.

23. A method of chiral synthesis comprising contacting a P-chiral compound of claim 18 with a substrate.

24. A P-chiral compound of claim 18 in which each of the two the phosphorous atoms is further substituted with a $BH_3$ radical.

25. The method of claim 23 wherein the chiral synthesis is asymmetric hydrogenation.

26. A P-chiral compound according to claim 18, wherein $R_{21}$ and $R_{26}$ are phenyl and $R_{25}$ and $R_{30}$ are hydrogen; and $R_{22}$, $R_{23}$, $R_{24}$, $R_{27}$, $R_{28}$ and $R_{29}$ are independently selected from hydrogen, $C_{1-4}$ alkyl, $CF_3$, $C_{1-4}$ alkoxy, phenyl and benzyloxy.

27. A P-chiral compound according to claim 18, wherein $R_{21}$ and $R_{26}$ are phenyl and $R_{22}$, $R_{23}$, $R_{24}$, $R_{25}$, $R_{27}$, $R_{28}$, $R_{29}$ and $R_{30}$ are hydrogen.

28. A P-chiral compound according to claim 18 selected from (R,R)-1,2-Bis[phenyl-(2-biphenyl) phosphino]ethane and (S,S)-1,2-Bis[phenyl-(2-biphenyl)phosphino]ethane.

29. A P-chiral compound according to claim 18, wherein $R_{21}$ and $R_{26}$ are benzyloxy and $R_{25}$ and $R_{30}$ are hydrogen; and $R_{22}$, $R_{23}$, $R_{24}$, $R_{27}$, $R_{28}$ and $R_{29}$ are independently selected from hydrogen, $C_{1-4}$ alkyl, $CF_3$, $C_{1-4}$ alkoxy, phenyl and benzyloxy.

30. A P-chiral compound according to claim 18, wherein $R_{21}$ and $R_{26}$ are benzyloxy and $R_{22}$, $R_{23}$, $R_{24}$, $R_{25}$, $R_{27}$, $R_{28}$, $R_{29}$ and $R_{30}$ are hydrogen.

31. A P-chiral compound according to claim 18 selected from (R,R)-1,2-Bis[phenyl-(2-benzyloxy-phenyl) phosphino]ethane and (S,S)-1,2-Bis[phenyl-(2-benzyloxy-phenyl) phosphino]ethane.

\* \* \* \* \*